United States Patent [19]

Boberg et al.

[11] 4,438,114
[45] Mar. 20, 1984

[54] β-LACTAM ANTIBIOTICS

[75] Inventors: Michael Boberg; Dieter Häbich; Karl G. Metzger; Paul Naab, all of Wuppertal, Fed. Rep. of Germany

[73] Assignee: Bayer Aktiengesellschaft, Leverkusen, Fed. Rep. of Germany

[21] Appl. No.: 415,632

[22] Filed: Sep. 7, 1982

[30] Foreign Application Priority Data

Sep. 17, 1981 [DE] Fed. Rep. of Germany ....... 3137038

[51] Int. Cl.³ .................. A61K 31/535; C07D 498/04
[52] U.S. Cl. .......................... 424/248.51; 424/248.52; 424/248.54; 544/90
[58] Field of Search ..................... 544/90; 424/248.51, 424/248.52, 248.54; 542/420

[56] References Cited

U.S. PATENT DOCUMENTS

| | | | |
|---|---|---|---|
| 4,147,693 | 4/1979 | König et al. | 542/420 X |
| 4,200,576 | 4/1980 | Feyer et al. | 542/420 X |
| 4,338,434 | 7/1980 | Preiss et al. | 542/420 |

FOREIGN PATENT DOCUMENTS 2739448  3/1978  Fed. Rep. of Germany .

OTHER PUBLICATIONS

Journal of the American Chemical Society /96:24/ Nov. 27, 1974, pp. 7582–7584.
The Synthesis of Oxygen Analogs of Cepham. A New Bicyclic System Department of Chemistry, Mass. Institute of Technology, Dec. 1968, vol. 5, pp. 779–783.
Communications, Dept. of Chem. Queen's Univ., Kingston, Ontario, pp. 3996–3999.

*Primary Examiner*—Richard Raymond
*Attorney, Agent, or Firm*—Sprung, Horn, Kramer & Woods

[57] ABSTRACT

A β-lactam of the formula

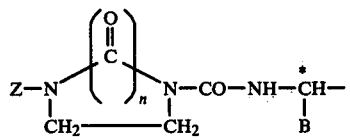

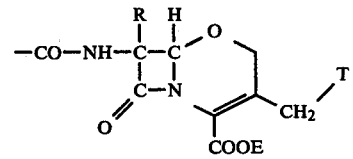

or a hydrate thereof, in which

R represents a hydrogen atom or a methoxy group,
n is 1 or 2,
Z represents a group of the formula

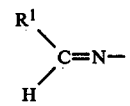

wherein $R^1$ denotes an optionally substituted aryl group or an optionally substituted heterocyclyl group;

or, when n is 1,

Z can also represent an optionally substituted cycloalkyl group or an optionally substituted pseudoaromatic heterocyclic 5-membered or 6-membered ring, B represents an optionally substituted phenyl or cyclohexadienyl group, or an unsaturated optionally subtituted heterocyclic ring, T denotes an alkyl—CO—O—, pyridinium, aminopyridinium, carbamoylpyridinium or carbamoyloxy group, an —S—phenyl group which can be substituted, or an —S—Het group in which Het represents an optionally substituted heterocyclic 5-membered or 6-membered ring; and E represents a hydrogen atom, a pharmaceutically acceptable ester grouping a salt-forming cation or a protective group, or represents a negative charge when T contains a quaternary nitrogen, which possesses antibacterial activity rendering it useful as an antibiotic and animal feed supplement.

12 Claims, No Drawings

β-LACTAM ANTIBIOTICS

The present invention relates to certain new β-lactam antibiotics, to processes for their production and to their use as antibacterial agents and as agents for promoting growth and for improving the utilization of feed in animals.

It has already been disclosed that certain α-(imidazolidin-2-oxo-1-yl-carbonylamino)-benzylpencillins and the corresponding cephalosporins with an imidazolidin-2-oxo-1-yl-carbonylamino side chain have antibacterial activity (U.S. application Ser. No. 692,877 filed June 4, 1976, now pending, and Pat. Nos. 4,147,693 and 4,338,434).

Cephalosporin analogues having an oxygen atom instead of the sulphur atom in the six-membered ring are described in the Journal of Heterocyclic Chemistry, Vol. 5 (1968), page 779, Canadian Journal of Chemistry, Vol. 52 (1974), page 3996, and J. Am. Chem. Soc., Vol. 96 (1974), page 7582.

Surprisingly, the oxacephemes of the present invention possess superior properties in respect of their action in comparison with the specific penicillins and cephalosporins described in the abovementioned U.S. Applications.

The present invention now provides, as new compounds, β-lactam antibiotics which are of the general formula

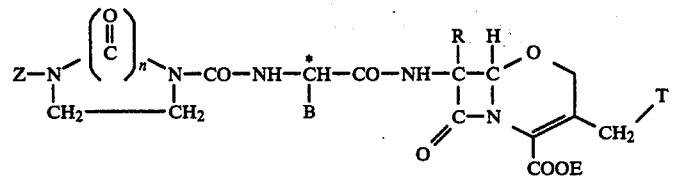

(I)

or salts or hydrate forms thereof,
in which
R represents a hydrogen atom or a methoxy group,
n is 1 or 2,
z represents a group of the general formula

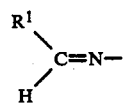

(Ia)

wherein $R^1$ denotes an optionally substituted aryl group or an optionally substituted heterocyclyl group;
or when n is 1,
Z can also represent an optionally substituted cycloalkyl group or an optionally substituted pseudoaromatic heterocyclic 5-membered or 6-membered ring,
B represents an optionally substituted phenyl or cyclohexadienyl group, or an unsaturated optionally substituted heterocyclic ring,
T denotes an alkyl—CO—O—, pyridinium, aminopyridinium, carbamoylpyridinium or carbamoyloxy group, a group —S—phenyl, which can be substituted, or a group —S—Het, in which Het represents an optionally substituted heterocyclic 5-membered or 6-membered ring; and
E represents a hydrogen atom, a pharmaceutically acceptable ester grouping (such as the pivaloyloxymethyl group), a salt-forming cation or a suitable protective group, or represents a negative charge when T contains a quaternary nitrogen, and the compounds of the formula (I) can be present in the two possible R and S configurations with respect to the center of chirality C*, and as mixtures of the diastereomers resulting therefrom, and, if Z represents the group of formula (Ia), the compounds of the formula (I) can be present both in the syn form and in the anti form with respect to the amino group.

The compounds of the present invention have powerful antibacterial properties and which possess properties for improving growth and the utilization of feed in animals.

Preferred compounds of the present invention are those in which
R represents a methoxy group,
n is 1 or 2,
Z represents the group of formula (Ia), as defined above,
wherein
$R^1$ denotes a phenyl group which is optionally substituted by halogen (especially fluorine, chlorine and bromine), alkyl having 1 to 4 carbon atoms (especially methyl), alkoxy having 1 to 4 carbon atoms, (especially methoxy), nitro, cyano, 1 or 2 hydroxyl groups, S-alkyl having 1 to 4 carbon atoms (especially S-methyl), alkylsulphonyl having 1 to 4 carbon atoms (especially methylsulphonyl) or $CH_3OOC$—; denotes a thienyl or furyl group which is optionally substituted (preferably in the 4-position or 5-position) by halogen (especially chlorine or bromine), $NO_2$, alkyl or alkoxycarbonyl having 1 to 4 carbon atoms, S—$C_1$ to $C_4$ alkyl, $C_1$ to $C_4$ alkylsulphonyl (especially methylsulphonyl), $C_1$–$C_4$-alkylsulphinyl (especially methylsulphinyl) or $CH_3COOCH_2$—, (the furyl ring and thienyl ring preferably being bonded in the 2-position or 3-position), or denotes a pyridyl group (preferably a pyrid-3-yl group);
or when
n is 1,
Z can also represent a cyclopropyl, furyl, pyridyl, thienyl or benzthiazol-2-yl radical, or a 1,3,4-thiadiazol-2-yl radical which is optionally substituted in the 5-position by sec.-butyl, trifluoromethyl, methylthio, i-propylthio or methylsulphonyl,
B represents a phenyl, hydroxyphenyl, cyclohexadienyl, furyl, thienyl, pyrrolyl, imidazolyl, thiazolyl, isothiazolyl, isoxazolyl or thiadiazolyl group,
T represents —$OCOCH_3$, or a tetrazolylthio or thiadiazolylthio group which is optionally substituted by alkyl having 1 to 4 carbon atoms, by $CF_3$ or by $CH_2COOH$, or represents a pyridinium, aminopyridinium, carbamoylpyridinium, carbamoyloxy or 1,2,5,6-tetrahydro-2-methyl-5,6-dioxo-asym-triazin-3-yl-thio group, and C* is present in the D—=R configuration.

According to the present invention we further provide a process for the production of a compound of the present invention in which (a) a compound of the general formula

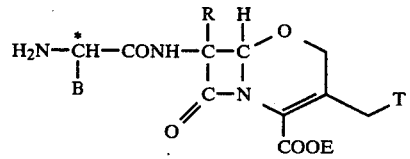

in which

R, B, C*, T and E have the meanings given above, or a derivative thereof which is silylated at the carboxyl and amino group or only at the carboxyl group, is reacted with a compound of the general formula

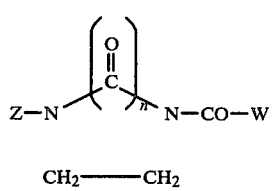

in which

Z and n have the meanings given above and

W represents halogen, azide or another nucleofugic leaving group, in the presence of a solvent and, if appropriate, of an acid-binding agent, at a temperature between $-70°$ C. and $+50°$ C., or (b), if a compound of formula (I) is required in which R represents a methoxy group, a compound of the general formula

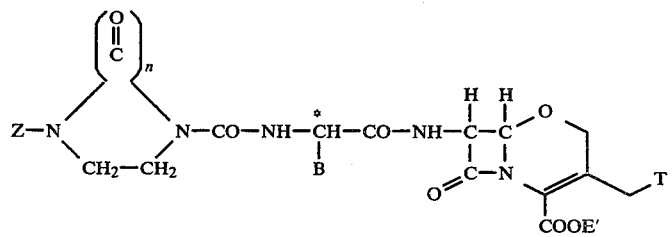

in which

Z, n, C*, B and T have the meanings given above, and

E' has any of those meanings given above for E or represents a protective group, is reacted with 1 to 10 equivalents of a base per equivalent of the β-lactam antibiotic of the formula (IV), in the presence of an excess of methanol in an inert organic solvent, with the addition of an N-halogenating agent, and the compound of formula (I) is isolated, if necessary after previously splitting off the protective group, or (c) a compound of the general formula

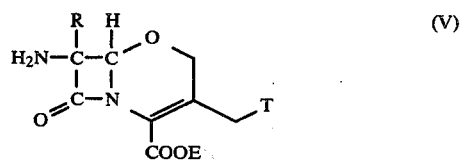

in which

R, T and E have the meanings given above, or a derivative thereof activated at the 7-amino group, is reacted with an acylating agent of the general formula

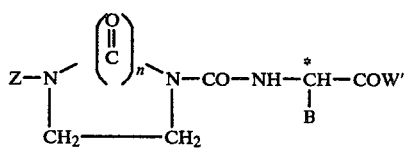

in which

Z, n, C* and B have the meanings given above and

W' is OH or a reactive leaving group, or (d) a compound of the general formula

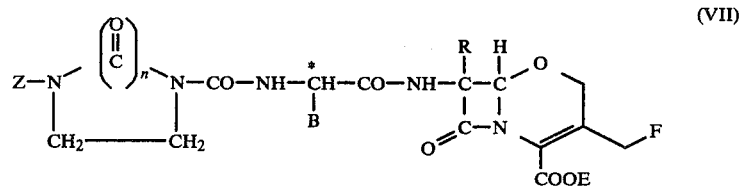

in which

Z, n, C*, B, R and E have the meanings given above and

F represents a group which can be split off under the reaction conditions, is reacted with a substance of the general formula $$R^2M \qquad (VII)$$

in which

R² represents an organic group, corresponding to (IV)

radical T as defined above, which is linked via O, N or S, and

M denotes a hydrogen atom, an alkali metal or an alkaline earth metal, or with a tertiary amine, so as to replace the radical F by a radical T, in which T has the meaning given above, and the β-lactam antibiotic obtained by reaction variant (a), (b), (c) or (d) is converted, if desired into a salt thereof, or the free acid is prepared from the salt obtained.

In reaction variant (c), the 7-amino group of the compound of formula (V) can be activated before the reaction, for example in the form of an isocyano, isocyanate, 1-halogenoalkylideneamino, 1-alkoxyalkylideneamino, silylamino orr enamine group. Free acids, acid-halides, acid anhydrides, active esters, active amides and ketenes having the desired acyl radical are examples of suitable compounds of formula (VI). The acylation can be carried out, if appropriate, in the presence of a base (such as triethylamine, pyridine or sodium bicarbonate), molecular sieves, carbodiimides (for example dicyclohexylcarbodiimide), epoxides (for example propylene oxide or butylene oxide) or enzymes. The reaction can be effected according to the acid-chloride, acid anhydride, carbodiimide or active ester method.

In reaction variant (d), F denotes a substituent which can readily be replaced by a nucleophilic agent, for example a halogen atom, as well as groups such as formyloxy, acetoxy, propionyloxy, butyryloxy, pivaloyloxy or —OCOCHCl$_2$; an arylcarbonyloxy group, such as benzoyloxy or naphthoyloxy; an arylcarbonylthio group, such as benzoylthio or naphthoylthio; a carbamoyl group; or a heteroaromatic N-oxoaminothio group with a mercapto group at the carbon atom adjacent to the N-oxide group in the molecule, such as 1-oxopyrid-2-ylthio or 1-oxopyridazine-6-ylthio. Each of the groups can be substituted by one or more substituents, for example halogen, nitro, alkyl, alkoxy, alkylthio or acyl.

In the formula (VIII), $R^2$ denotes the mentioned organic group which is linked via O, N or S, and M denotes a hydrogen atom, an alkali metal or an alkaline earth metal. The tertiary amine employed can be amines such as pyridine, quinoline, isoquinoline or pyrimidine. These tertiary amines can be substituted by one or more substituents, such as halogen, lower alkyl or carbamoyl.

In the compounds of the present invention and the corresponding starting materials, radical $R^1$, when optionally substituted aryl, represents an aryl group preferably having 6 to 10 carbon atoms in the aryl part. Optionally substituted phenyl or naphthyl may be mentioned as examples. Substituents in the phenyl ring are in the o-, m- or p-position. Furthermore, the radicals

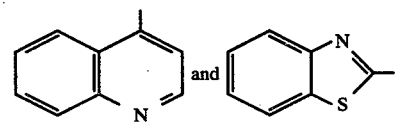

may be mentioned. Radical $R^1$, when optionally substituted heterocyclyl, preferably represents a heteroparaffinic, heteroaromatic and heteroolefinic 5-membered to 7-membered, preferably 5-membered or 6-membered, rings having preferably 1 to 3, in particular 1 or 2, identical or different hetero atoms selected from oxygen, sulphur and nitrogen. Optionally substituted thienyl, furyl, oxazolyl, isoxazolyl, thiazolyl, isothiazolyl, pyrrolyl, imidazolyl, pyrazolyl, oxadiazolyl, thiadiazolyl, triazolyl, oxatriazolyl, thiatriazolyl, tetrazolyl, pyridyl, pyrazinyl, pyrimidinyl, tetrahydrofuranyl, dioxanyl, pyrrolidinyl, piperidinyl, morpholinyl, pyron-2-yl and pyron-4-yl are examples.

$R^1$, when aryl, can carry one or more, preferably 1 to 3, in particular 1 or 2, identical or different radicals $R^3$, as defined below. Very particularly preferably, the radicals $R^1$ mentioned are unsubstituted or contain one substituent $R^3$.

$R^1$, when heterocyclyl, can carry one or more, preferably 1 to 3, in particular 1 or 2, identical or different radicals $R^4$, as defined below. Very particularly preferably, heterocyclyl $R^1$ is unsubstituted or contains one substituent $R^4$.

In the descriptions which follow, the expression "lower alkyl" denotes throughout, even in a compound with other atoms or groups (such as lower alkoxy or HCON—(lower alkyl)), straight-chain or branched alkyl having preferably 1 to 6, especially 1 to 4, carbon atoms. Optionally substituted methyl, ethyl, n- and i-propyl, n-, i- and t-butyl may be mentioned as examples. "Lower alkyl" can be substituted by 1 to 5, in particular 1 to 3, identical or different halogen atoms, the halogen atoms preferably being fluorine, chlorine and bromine, especially fluorine. Trifluoromethyl, chlorodifluoromethyl, bromomethyl, 2,2,2-trifluoroethyl and pentafluoroethyl may be mentioned as examples.

$R^3$ preferably denotes halogen, preferably fluorine, chlorine, bromine and iodine, in particular fluorine, chlorine and bromine; amino; mono-lower alkylamino, preferably methylamino, and ethylamino, in particular methylamino; di-lower alkylamino, preferably dimethylamino and diethylamino, in particular dimethylamino; pyrrolidyl; piperidyl; HCO—NH—, lower alkyl—CO—NH—, preferably CH$_3$—CO—NH—; H—CO—N(lower alkyl)—, preferably H—CO—N(CH$_3$)—, H—CO—N(C$_2$H$_5$)—; lower alkyl—CO—N(lower alkyl)—, preferably CH$_3$—CO—N(CH$_3$)—; (lower alkyl)$_2$C=N—; lower alkyl—SO$_2$—NH—, preferably CH$_3$—SO$_2$—NH—, C$_2$H$_5$—SO$_2$—NH—, in particular CH$_3$—SO$_2$—N(CH$_3$)—; HO—SO$_2$—NH—; HO—SO$_2$—N(lower alkyl)—, preferably HO—SO$_2$N(CH$_3$)—, HO—SO$_2$—N(C$_2$H$_5$)—; amidino; (lower alkyl)$_2$—N—CH=N—, in particular (CH$_3$)$_2$N—CH=N—;

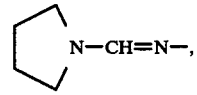

guanido, nitro, azido, hydroxy, lower alkyloxy—, preferably CH$_3$—O—, C$_2$H$_5$—O—, in particular CH$_3$O—, H—CO—O—, lower alkyl—CO—O—, preferably CH$_3$—CO—O—, C$_2$H$_5$—CO—O—, (CH$_3$)$_3$C—CO—O—; lower alkyl—O—CO—O—, preferably CH$_3$—O—CO—O—, C$_2$H$_5$—O—CO—O—, (CH$_3$)$_3$C—O—CO—O; H$_2$N—CO—O—; lower alkyl—NH—CO—O—, preferably CH$_3$—NH—CO—O—, C$_2$H$_5$—NH—CO—O—, (lower alkyl)-$_2$N—CO—O— preferably (CH$_3$)$_2$N—CO—O—, (C$_2$H$_5$)$_2$N—CO—O—,

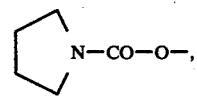

H₂N—SO₂—O—; lower alkyl—NH—SO₂—O—, preferably CH₃—NH—SO₂—O—, C₂H₅—NH—SO₂—O—; (lower alkyl)₂N—SO₂—O—, preferably (CH₃)₂N—SO₂—O—, (C₂H₅)₂N—SO₂—O—; HOOC—; H₂N—CO—; (lower alkyl)₂N—CO, in particular (CH₃)₂N—CO— and (C₂H₅)₂N—CO—; OHC—, HO—SO₂—O—, HS—; lower alkyl—S—, preferably CH₃—S—, CF₃—S—, C₂H₅—S—, (CH₃)₂—CH—S—;

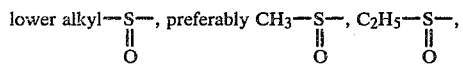

HO₃S—, lower alkyl—SO₂—, preferably CH₃—SO₂—, CF₃SO₂—, C₃H₅—SO₂—; the group H₂N—SO₂—, lower alkyl—NH—SO₂—, preferably CH₃—NH—SO₂—, C₂H₅—NH—SO₂—; (lower alkyl)₂-N—SO₂—, preferably (CH₃)₂N—SO₂—, (C₂H₅)₂N—SO₂—; the group HO—SO₂—S—; straight-chain or branched alkyl having 1 to 6 carbon atoms, in particular methyl, ethyl, propyl, isopropyl, n-butyl, sec.-butyl or tert.-butyl, preferably methyl; and phenyl or phenoxy.

In the case in which R⁴ is located at one or more carbon atoms in the heterocyclyl R¹, R⁴ preferably denotes lower alkyl, preferably methyl, ethyl, isopropyl, in particular methyl; the group trifluoromethyl; halogen, preferably fluorine, chlorine and bromine; amino; lower alkylamino, preferably CH₃—NH— and C₂H₅—NH—; di-lower alkylamino, preferably (CH₃)₂N—, (C₂H₅)₂N—; formylamino; acetylamino; CH₃—O—CO—NH—, C₂H₅O—CO—NH—; CH₃—SO₂—NH—; hydroxy; methoxy; ethoxy; methylthio, ethylthio; CH₃—SO₂—; CH₃—SO—; the groups HOOC—; HO₃S—; HCO—; lower alkyl—CO—, preferably CH₃—CO—; lower alkyl—O—CO—, preferably CH₃—O—CO—, C₂H₅O—CO—; and —CN.

In the case in which R⁴ is the substituent at one or more nitrogen atoms in a nitrogen-containing heterocyclyl R¹, R⁴ preferably denotes lower alkyl, preferably methyl, etthyl, propyl and isopropyl, in particular methyl and ethyl; the group —C⁻=N; —CHO; —COO—lower alkyl, preferably —COO—CH₃, —COOC₂H₅, —COOCH(CH₃)₂, —COO—C(CH₃)₃; —CO—NH₂; —CO—NH—lower alkyl, preferably —CO—NH—CH₃, —CO—NH—C₂H₅, —CO—NH—CH(CH₃)₂; and —CO—lower alkyl, preferably —CO—CH₃, —CO—C₂H₅, —CO—CH(CH₃)₂.

In the formulae, optionally substituted cycloalkyl Z denotes that having 3 to 7, preferably 3 to 6, ring carbon atoms. The following may be mentioned as examples: cyclopropyl, cyclobutyl, cyclopentyl and cyclohexyl.

The following may be mentioned as examples of optionally substituted pseudoaromatic heterocyclic 5-membered or 6-membered rings Z: furyl (preferably fur-2-yl), pyrrl (preferably pyrr-2-yl); 1-methylpyrr-2-yl or 1-methylpyrr-3-yl; thienyl (preferably thien-2-yl); oxazolyl (bonded in the 2-, 4- or 5-position); thiazolyl (bonded in the 2-, 4- or 5-position); isoxazolyl (bonded in the 3-, 4- 5-position); isothiazolyl (bonded in the 3-, 4- or 5-position) 1,2,5-oxadiazol-3-yl; 1,2,5-thiadiazol-3-yl; 1,3,4-oxadiazol-2-yl; 1,3,4-thiadiazol-2-yl; 1,2,4-oxadiazolyl (bondded in the 3- or 5-position); 1,2,4-thiadiazolyl (bonded in the 3- or 5-position); pyrazolyl (bonded in the 3-, 4- or 5-position); 1,2,4-triazolyl (bonded in the 3- or 5-position); tetrazolyl; pyridyl (bonded in the 2-, 3- or 4-position); pyridazinyl (bonded in the 3- or 4-position); pyrimidinyl (bonded in the 2-, 4- or 5-position); α-pyronyl (bonded in the 3-, 4-, 5- or 6-position); α-pyronyl (bonded in the 3-, 4-, 5- or 6-position); α-pyronyl (bonded in the 2- or 3-position); benzthiazol-2-yl, and thiazolyl (bonded in the 2-, 4-, or 5-position).

Cycloalkyl Z, and heterocyclic 5-membered or 6-membered rings Z, can be monosubstituted, disubstituted or trisubstituted, preferably monosubstituted or disubstituted, in particular monosubstituted. The following may be mentioned as examples of substituents: lower alkyl, in particular methyl, ethyl, propyl, isopropyl and t-butyl, preferably methyl; lower alkylidene, in particular methylidene, ethylidene and isopropylidene; vinyl, propenyl, allyl and isopropenyl; lower alkoxymethyl, in particular methoxymethyl; lower alkylthiomethyl, in particular methylthiomethyl; trifluoromethyl; hydroxymethyl; formyl; lower alkanoyl, in particular acetyl; lower alkanoyloxymethyl, in particular acetoxymethyl; benzyl; aryl, in particular phenyl; cyanomethyl; the groups CH₃—NH—CO—CH₂— and (CH₃)₂N—CO—CH₂—; lower alkoxycarbonyl, in particular methoxycarbonyl and ethoxycarbonyl; carboxyl; cyano; hydroxyl; lower alkanoyloxy, in particular acetoxy; lower alkoxy, in particular methoxy and ethoxy; benzyloxy; halogen, in particular fluorine, chlorine and bromine, preferably chlorine; mercapto; lower alkylthio, in particular methylthio and ethylthio; lower alkylsulphinyl, in particular methylsulphinyl and ethylsulphinyl; lower alkylsulphonyl, in particular methylsulphonyl and ethylsulphonyl; and the groups CH₃—CO—NH—, CH₃—CO—N(CH₃)—, CH₂—SO₂—NH— and

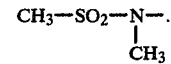

The cycloalkyl radicals Z are preferably unsubstituted, the unsubstituted cyclopropyl radical, in particular, being singled out.

The heterocyclic 5-membered or 6-membered rings Z are very particularly preferably unsubstituted or monosubstituted, lower alkyl, trifluoromethyl, lower alkylsulphonyl, lower alkylthio and trifluoromethyl being mentioned as preferred substituents. The following may be mentioned as particularly preferred heterocyclic rings Z: pyrid-2-yl, pyrid-3-yl or pyrid-4-yl; furyl; 5-methylthio-(1,3,4-thiadiazol)-2-yl; 5-i-propylthio-(1,3,4-thiadiazol)-2-yl; 5-methylsulphonyl-(1,3,4-thiadiazol)-2-yl; 5-trifluoromethyl-(1,3,4--thiadiazol)-2-yl, 5-trifluoromethyl-(1,3,4-thiadiazol)-2-yl; 5-sec.-butyl-(1,3,4-thiadiazol)-2-yl and benzthiazol-2-yl.

B represents a saturated or unsaturated, but preferably unsaturated, optionally substituted heterocyclic radical which can contain 1 to 4, but preferably 1 to 3, identical or different hetero atoms from the series comprising oxygen, sulphur and/or nitrogen.

The following may be mentioned as examples of suitable radicals of this type: pyrazolyl, imidazolyl, oxazolyl, oxadiazolyl, 2-amino-thiazolinyl and 2-oxo-Δ⁴-thiazolinyl, tetrazolyl, sydnonyl and furyl, thienyl, pyrrolyl, thiazolyl, isothiazolyl, isoxazolyl and thiadiazolyl radicals. The heterocyclic radical B can carry one or more, preferably 1 to 2, identical or different substituents. Halogen, such as fluorine, chlorine or bromine, preferably fluorine and chlorine, alkyl having 1 to 6, preferably 1 to 4, in particular 1 or 2, carbon atoms; cyano, sulphonyl and methylsulphonyl may be mentioned as examples of substituents.

Phenyl B can carry one or more, preferably 1 to 3, in particular 1 or 2, identical or different substituents. The substituents can be in the o-, m- and/or p-position. A substituent is preferably located in the p- or m-position. Halogen, such as fluorine, chlorine, bromine and iodine, preferably fluorine, chlorine and bromine; alkyl having 1 to 6, preferably 1 to 4, in particular 1 or 2, carbon atoms; cyano and methylsulphonyl may be mentioned as examples of substituents. In particular, the hydroxyphenyl radical (preferably p-hydroxyphenyl), the methylphenyl radical (preferably p-methylphenyl), the cyanophenyl radical (preferably m- and p-cyanophenyl), the methylsulphonylphenyl radical (preferably p-methylsulphonylphenyl) and the fluorophenyl radical (preferably o-fluorophenyl and m-fluorophenyl) may be mentioned as substituted phenyl radicals B.

In the definition of T, alkyl in alkyl—CO—O— preferably denotes alkyl having 1 to 4, in particular 1 or 2, carbon atoms. Methyl and ethyl may be mentioned as examples, methyl being particularly preferred.

The heterocyclic ring Het in —S—HET (definition of T) consists of 5 or 6 ring members and contains 1 to 4, preferably 3 to 4, identical or different hetero atoms, the hetero atoms being oxygen, sulphur and nitrogen. The heterocyclic ring is preferably unsaturated and particularly preferably contains 2 double bonds. The heterocyclic ring can contain one or more, preferably 1 or 2, in particular one, substituent. The following may be mentioned as examples of substituents: halogen, such as fluorine, chlorine and bromine, preferably chlorine and bromine, amino, lower alkylamino, di-lower alkylamino, lower alkyl, cycloalkyl (having 3 to 7, preferably 5 or 6, carbon atoms in the cycloalkyl part), lower alkoxy (see above for the meaning of "lower alkyl"), trifluoromethyl, phenyl, benzyl and acylamino having preferably 2 to 5, in particular 2 or 3, carbon atoms. The following may be particularly preferably mentioned as —S—Het:

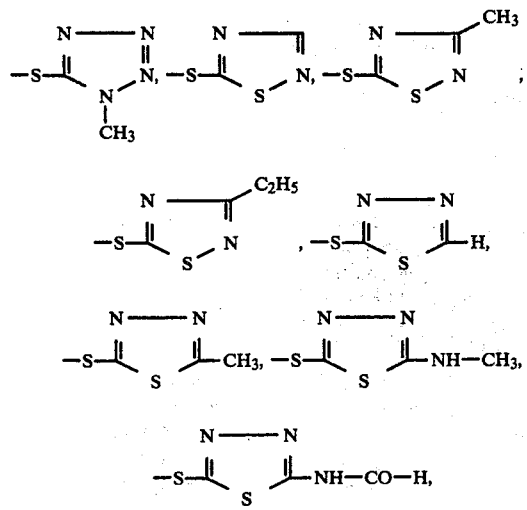

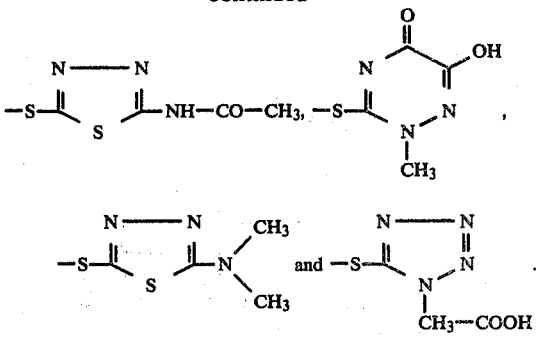

The —S—phenyl radical in the definition of T can carry one or more, preferably 1 to 3, in particular 1 or 2, identical or different substituents, those substituents which are mentioned above as possible substituents of the radical —S—Het being preferred.

Compounds according to the invention, in which C* is present in the D—=R configuration, are very particularly preferred.

All crystalline forms and hydrate forms of the compounds according to the invention, of the general formula (I), and their salts are antibacterially active in the same way.

Halogen W represents fluorine, chlorine and bromine, preferably bromine or chlorine, in particular chlorine.

Nucleofugic leaving groups in the definition of W are to be understood as meaning any of the nucleofugic groups customarily used in organic chemistry, for example those which are described in Angewandte Chemie, 81 (1969) page 543.

Among the new β-lactam antibiotic salts of the invention, those salts that are pharmaceutically acceptable are particularly important and are preferred.

The new free β-lactam antibiotics of the general formula (I) and their salts can be interconverted in any suitable manner; methods for such interconversion are known in the art.

Pharmaceutically acceptable salts of the compounds of the formula (I) are salts of these compounds with inorganic and organic bases at the acidic carboxyl group or the acidic carboxyl and sulphonic acid groups. For this purpose, any of the bases which are customarily used in pharmaceutical chemistry, in particular in the chemistry of antibiotics, can be employed as bases. The following may be mentioned as examples of inorganic bases: alkali metal hydroxides and alkaline earth metal hydroxides, alkali metal carbonates and alkaline earth metal carbonates and alkali metal bicarbonates (such as sodium hydroxide and potassium hydroxide, calcium hydroxide and magnesium hydroxide, sodium carbonate and potassium carbonate, calcium carbonate, sodium bicarbonate and potassium bicarbonate), aluminum hydroxide and ammonium hydroxide. Primary, secondary and tertiary aliphatic amines and heterocyclic amines can be employed as organic amines. The following may be mentioned as examples: di-lower alkylamines and tri-lower alkylamines, for example diethylamine, triethylamine, tri-β-hydroxyethylamine, procaine, dibenzylamine, N,N'-dibenzylethylenediamine, N-benzyl-β-phenylethylamine, N-methylmorpholine and N-ethylmorpholine, 1-ephenamine, dehydroabietylamine, N,N'-bis-dehydroabietylethylenediamine and N-(lower alkyl)piperidine. So-called basic aminoacids, such as lysine or arginine, can also advantageously be used as bases. The sodium salts are particularly preferred salts.

The term "lower alkyl" is understood as meaning, in each case, both straight-chain and branched alkyl groups having 1 to 5, preferably 1 to 3, in particular 1 or 2, carbon atoms. In connection with other groups, such as "di-lower alkylamino", the term "-lower alkyl" refers only to the alkyl part of the particular group.

The compounds according to the invention exhibit, in addition to good toleration and solubility, a broad antibacterial action, that is to say an action against several families of bacteria in the Gram-negative and Gram-positive range, and against β-lactamase formers. Owing to their powerful antibacterial properties and because of their ability to improve the growth and the utilisation of feed in animals, the compounds according to the invention thus represent an enrichment of the art.

The active compounds according to the invention display a powerful antimicrobial activity, coupled with low toxicity and good toleration. These properties enable them to be used as active compounds in medicine and as substances for preserving inorganic and organic materials, especially organic materials of all kinds, for example polymers, lubricants, paints, fibers, leather, paper and timber, and foodstuffs and water.

The active compounds according to the invention are active against a very broad spectrum of microorganisms. With the aid of these compounds, it is possible, for example, to combat Gram-negative and Gram-positive bacteria and bacteria-like microorganisms and to prevent, alleviate and/or cure diseases caused by these pathogens.

The active compounds according to the invention are particularly active against bacteria and bacteria-like micro-organisms. They are therefor particularly susitable, in human medicine and veterinary medicine, for the propylaxis and chemotherapy of local and systemic infections caused by these pathogens.

For example, local and/or systemic diseases which are caused by the following pathogens or by mixtures of the following pathogens can be treated and/or prevented:

Micrococcaceae, such as Staphylococci, for example *Staphylococcus aureus, Staph. epidermidis* and *Staph. aerogenes* and *Gaffkya tetragena* (Staph.=Staphylococcus); Lactobacteriaceae, such as Streptococci, for example *Streptococcus pyogenes*, α- and β-haemolysing Streptococci, non-(γ-)-haemolysing Streptococci, *Str. viridans, Str. faecalis (Enterococci), Str. agalactiae, Str. lactis, Str. equi* and *Str. anaerobis*, and *Diplococcus pneumoniae (Pneumococci)* (Str.=Streptococcus): Neisseriaceae, such as Neisseriae, for example *Neisseria gonorrhoeae (Gonococci), N. meningitidis (Meningococci), N. catarrhalis* and *N. flava* (N.=Neisseria); and Corynebacteriaceae, such as Corynebacteria, for example *Corynebacterium diphtheriae, C. pyogenes, C. diphtheroides, C. acnes, C. parvum, C. bovis, C. renale, C. ovis* and *C. murisepticum,* Listeria bacteria, for example *Listeria monocytogenes,* Erysipelothrix bacteria for example *Erysipelothrix insidiosa,* Kurthia bacteria, for example *Kurthia zopfii* (C.=Corynebacterium); Enterobacteriacease, such as Escherichiae bacteria of the Coli group, Escherichia bacteria, for example *Escherichia coli,* Enterobacter bacteria, for example *E. aerogenes* and *E. cloacae,* Klebsiella bacteria, for example *K. pneumoniae* and *K. ozaenae,* Erwiniae, for example Erwinia spec., and Serratia, for example *Serratia marcescens* (E.=Enterobacter) (K.=Klebsiella), Proteae bacteria of the Proteus group, Proteus, for example *Proteus vulgaris, Pr. morganii, Pr. rettgeri* and *Pr. mirabilis,* (Pr.=Proteus), Providencia, for example Providencia sp., and Salmonelleae, Salmonella bacteria, for example *Salmonella paratyphi A* and *B, S. typhi, S. enteritidis, S. cholerae suis* and *S. typhimurium* (S.=Salmonella), and Shigella bacteria, for example *Shigella dysenteriae, Sh. ambigua, Sh. flexneri, Sh. boydii* and *Sh. sonnei* (Sh.=Shigella); Pseudomonadaceae, such as Pseudomonas bacteria, for example *Pseudomonas aeruginosa* and *Ps. pseudomallei* (Ps.=Pseudomonas), Aeromonas bacteria, for example *Aeromonas liquefaciens* and *A. hydrophila* (A.=Aeromonas); Spirillaceae, such as Vibrio bacteria, for example *Vibrio cholerae, V. proteus* and *V. fetus* (V.=Vibrio), Spirillum bacteria, for example *Spirillum minus;* Parvobacteriaseae or Brucellaceae, such as Pasteurelle bacteria, for example *Pasteurella multocida* and *Past. pestis (Yersinia),* Brucella bacteria, for example *Brucella abortus, Br. melitensis* and *Br. suis* (Br.=Brucella), Haemophilus bacteria, for example *Haemophilus influenzae, H. ducreyi, H. suis* and *H. canis, H. aegypticus* (H.=Haemophilus), Bordetella bacteria, for example *Bordetella pertussis* and *B. bronchiseptica* (B.=Bordetella), Moraxella bacteria, for example *Moraxella lacunata;* Bacterioidacea, such as Bacteroides bacteria, for example *Bacteroides fragilis* and *B. serpens* (B.=Bacteroides), Fusiforme bacterial, for example *Fusobacterium fusiforme* and Sphaerophorus bacteria, for example *sphaerophorus necrophorus* and *Sph. necroticus, Sph. pyrogenes* (Sph.=Sphaerophurus); Bacillaceae, such as aerobic spore-forming Bacillaceae, for example *Bacillus anthracis, B. subtilis* and *B. cereus* (B.=Bacillus), and anaerobic spore-forming Clostridia, for example *Clostridium perfringens, Cl. septicium, Cl. oedematiens, Cl. histolyticum, Cl. tetani* and *Cl. botulinim* (Cl.=Clostridium); Spirochaetaceae, such as Borrelia bacteria, for example *Borrelia recurrentia* and *B. vincentii* (B.=Borrelia), Treponema bacteria, for example *Treponema pallidum, Tr. pertinue, Tr. carateum* (Tr.=Treponema), and Leptospira bacteria, Leptospira interrogans, for example *Leptospira icterohaemorrhagiae, L. canicola, L. grippotyphosa, L. pomona, L. mitis,* and *L. bovis* (L.=Leptospira).

The above list of pathogens is merely illustrative.

Examples which may be mentioned of diseases which can be prevented, alleviated and/or curved by the active compounds according to the invention are: diseases of the respiratory passages and of the pharyngeal cavity; otitis; pharyngitis; pneumonia; peritonitis; pyelonephritis; cystitis; endocarditis; systemic infections, bronchitis; and arthritis.

As stated above, the invention also relates to the use in human and veterinary medicine of the compounds of the invention.

The present invention provides a pharmaceutical composition containing as active ingredient a compound of the invention in admixture with a solid or liquefied gaseous diluent, or in admixture with a liquid diluent other than a solvent of a molecular weight less than 200 (preferably less than 350) except in the presence of a surface active agent.

The invention further provides a pharmaceutical composition containing as active ingredient a compound of the invention in the form of a sterile and/or physiologically isotonic aqueous solution.

The invention also provides a medicament in dosage unit form comprising a compound of the invention.

The invention also provides a medicament in the form of tablets (including lozenges and granules), dragees, capsules, pills, ampules or suppositories comprising a compound of the invention.

"Medicament" as used in this specification means physically discrete coherent portions suitable for medical administration. "Medicament in dosage unit formed" as used in this specification means physically discrete coherent units suitable for medical administration each containing a daily dose or a multiple (up to four times) or submultiple (down to a fortieth) of a daily dose of the compound of the invention in association with a carrier and/or enclosed within an envelope. Whether the medicament contains a daily dose or, for example, a half, a third or a quarter of a daily dose will depend on whether the medicament is to be administered once or, for example, twice, three times or four times a day respectively.

The pharmaceutical composition according to the invention may, for example, take the form of ointments, gels, pastes, creams, sprays (including aerosols), lotions, suspensions, solutions and emulsions of the active ingredient in aqueous or non-aqueous diluents, syrups, granulates or powders.

The diluents to be used in pharmaceutical compositions (e.g. granulates) adapted to be formed into tablets, dragees, capsules and pills include the following: (a) fillers and extenders, e.g. starch, sugars, mannitol, and silicic acid; (b) binding agents, e.g. carboxymethyl cellulose and other cellulose derivatives, alginates, gelatine and polyvinyl pyrrolidone; (c) moisturizing agents, e.g. glycerol; (d) disintegrating agents, e.g. agar-agar, calcium carbonate and sodium bicarbonate; (e) agents for retarding dissolution e.g. paraffin; (f) resorption accelerators, e.g. quaternary ammonium compounds; (g) surface active agents, e.g. cetyl alcohol, glycerol monostearate; (h) adsorptive carriers, e.g. kaolin and bentonite; (i) lubricants, e.g. talc, calcium and magnesium stearate and solid polyethyl glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in microencapsulated form together with one or several of the above-mentioned diluents.

The diluents to be used in pharmaceutical compositions adapted to be formed into suppositories can, for example, be the usual water-soluble diluents, such as polyethylene glycols and fats (e.g. cocoa oil and high esters (e.g. $C_{14}$-alcohol with $C_{16}$-fatty acid)) or mixtures of these diluents.

The pharmaceutical compositions which are ointments, pastes, creams and gels can, for example, contain the usual diluents, e.g. animal and vegetable fats, waxes, paraffins, starch, tragacanth, cellulose derivatives, polyethylene glycols, silicones, bentonites, silicic acid, talc and zinc oxide or mixtures of these substances.

The pharmaceutical compositions which are powders and sprays can, for example, contain the usual diluents, e.g. lactose, talc, silicic acid, aluminum hydroxide, calcium silicate, and polyamide powder or mixtures of these substances. Aerosol sprays can, for example, contain the usual propellants, e.g. chlorofluorohydrocarbons.

The pharmaceutical compositions which are solutions and emulsions can, for example, contain the customary diluents (with, of course, the above-mentioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils (for example ground nut oil), glycerol, tetrahydrofurfuryl alcohol, polyethylene glycols and fatty acid esters of sorbitol or mixtures thereof.

For parenteral administration, solutions and emulsions should be sterile, and, if appropriate, blood-isotonic.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitan esters), microcrystalline cellulose, aluminum metahydroxide, bentonite, agar-agar and tragacanth or mixtures thereof.

All the pharmaceutical compositions according to the invention can also contain coloring agents and preservatives as well as perfumes and flavoring additions (e.g. peppermint oil and eucalyptus oil) and sweetening agents (e.g. saccharin).

The pharmaceutical compositions according to the invention generally contain from 0.1 to 99.5% usually from 0.5 to 95% of the active ingredient by weight of the total composition.

In addition to a compound of the invention, the pharmaceutical compositions and medicaments according to the invention can also contain other pharmaceutically active compounds. They may also contain a plurality of compounds of the invention.

Any diluent in the medicaments of the present invention may be any of those mentioned above in relation to the pharmaceutical compositions of the present invention. Such medicaments may include solvents of molecular weight less than 200 as sole diluent.

The discrete coherent portions constituting the medicament according to the invention will generally be adapted by virtue of their shape or packaging for medical administration and may be, for example, any of the following: tablets (including lozenges and granulates), pills, dragees, capsules, suppositories and ampules. Some of these forms may be made up for delayed release of the active ingredient. Some, such as capsules, include a protective envelope which renders the portions of the medicament physically discrete and coherent.

The preferred daily dose for administration of the medicaments of the invention is 750 mg to 15 g of active ingredient.

The production of the above-mentioned pharmaceutical compositions and medicaments is carried out by any method known in the art, for example, by mixing the active ingredient(s) with the diluent(s) to form a pharmaceutical composition (e.g. a granulate) and then forming the composition into the medicament (e.g. tablets).

This invention further provides a method of combating (including prevention, relief and cure of) the above-mentioned diseases in human and non-human animals, which comprises administering to the animals a compound of the invention alone or in admixture with a diluent or in the form of a medicament according to the invention.

It is envisaged that these active compounds will be administered perorally, parenterally (for example intramuscularly, intraperitoneally, subcutaneously and intravenously), rectally or locally, preferably parenterally, especially intravenously or intramuscularly. Preferred pharmaceutical compositions and medicaments are therefore those adapted for administration such as parenteral administration. Administration in the method of the invention is preferably parenteral administration.

In general it has proved advantageous to administer amounts of from 6 to 800 mg/kg, preferably from 15 to 30 mg/kg, of body weight per day to achieve effective results. Nevertheless, it can at times be necessary to deviate from those dosage rates, and in particular to do so as a function of the nature and body weight of the human or animal subject to be treated, the individual reaction of this subject to the treatment, the type of formulation in which the active ingredient is administered and the mode in which the administration is carried out, and the point in the progress of the disease or interval at which it is to be administered. Thus it may in some case suffice to use less than the above-mentioned minimum dosage rate, whilst other cases the upper limit mentioned must be exceeded to achieve the desired results. Where larger amounts are administered it can be advisable to divide these into several individual administrations over the course of the day.

An individual administration preferably contains the active compound or compounds according to the invention in amounts of 2 to 300 mg/kg, in particular 10 to 150 mg/kg, of body weight.

When used as feed additives, the new compounds can be administered in the customary manner, together with the feed or with the feed formulations or with the drinking water. By this means, it is possible to prevent an infection by Gram-negative or Gram-positive bacteria and also to achieve better utilisation of the feed.

The new β-lactam antibiotics are distinguished by powerful antibacterial actions, which have been tested in vivo and in vitro, and by oral resorbability.

In order to broaden the spectrum of action or to achieve a more powerful action, the β-lactam antibiotics according to the invention can, for example, also be combined with aminoglycoside antibiotics, such as gentamicin, sisomicin, kanamicin, amikacin or tobramicin.

The following examples illustrate processes for the production of compounds of the present invention (the symbol "Ph" in the formulae representing a phenyl radical).

EXAMPLE 1

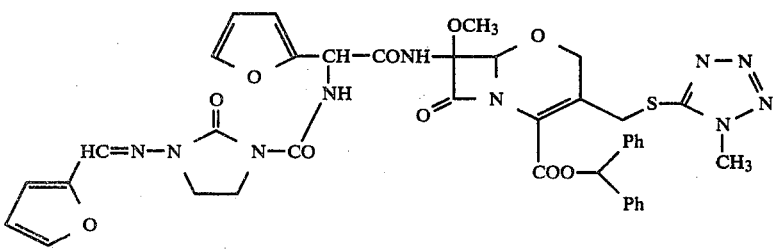

99 mg of 2-(2-oxo-3-furfurylideneamino-imidazolidin-1-yl)-carbonylamino-furylacetic acid were suspended in 1 ml of absolute acetone at room temperature, under a nitrogen atmosphere, and the suspension was treated with 1 ml of a solution of an equimolar amount of triethylamine in acetone. The mixture was cooled to $-25°$ C., a catalytic amount of dimethylaminopropanol was added, and thereafter 1 ml of a solution of 0.37 ml of isobutyl chloroformate diluted with acetone to 10 ml. This mixture was stirred for 3 hours at $-20°$ to $-15°$ C. In a separate operation, 29 mg of diphenylmethyl 7-methoxy-7-amino-3-(1-methyl-1-H-tetrazol-5-ylthiomethyl)-1-oxadethia-3-cephem-4-carboxylate were dissolved in 0.4 ml of absolute chloroform, 0.4 ml of acetone was added, and the mixture was cooled to $-15°$ C. 0.7 ml of the solution of the mixed anhydride was added to this solution, and the mixture was stirred for 2.5 hours at $-15°$ to $-10°$ C. and for a further 2.5 hours at $-10°$ to $-5°$ C. Working-up was effected by pouring the mixture into water, extracting (twice) with chloroform, and washing the organic phase with saturated sodium bicarbonate solution (twice) and water, drying it and concentrating it in vacuo. The residue was separated by preparative thin-layer chromatography, with benzene/methyl acetate (1:2) as the mobile phase: 10 mg of diphenylmethyl 7-methoxy-7-{DL-α-(2-oxo-3-furfurylidene-amino-imidazolidin-1-yl)-carbonylaminofurylacetamide}-3-(1-methyl-1-H-tetrazol-5-ylthiomethyl)-1-oxadethia-3-cephem-4-carboxylate.

$^1$H-NMR inter alia CDCl$_3$250 MHz: 3.48 and 3.56 (2s, 3H); 3.83, 386 and 3.6–4.0 (2s and m, 7H); 4.30 (s, 2H); 4.58 and 4.62 (2 AB systems, 2H); 5.04 and 5.10 (2s, 1H); 5.72 and 5.76 (2d, J=6 Hz, 1H); 6.3–6.5 (m, 3H); 6.7–6.8 (m, 1H); 6.90 (s. 1H); 7.06 and 7.08 (2s, 1H); 7.2–7.6 (m, 12H); 7.74 and 7.77 (2s, 1H); 9.02 and 9.06 (2d, J=6 Hz, 1H).

IR cm$^{-1}$ inter alia CHCl$_3$: 3600–3150 w, 3030–2850 w, 1790 s, 1740–1720 s, 1690 m, 1490 s, 1415 s, 1400 s, 1270 s, 1340–1210 s, 1080 m, 1025 m, 915 m, 705 m.

EXAMPLE 2

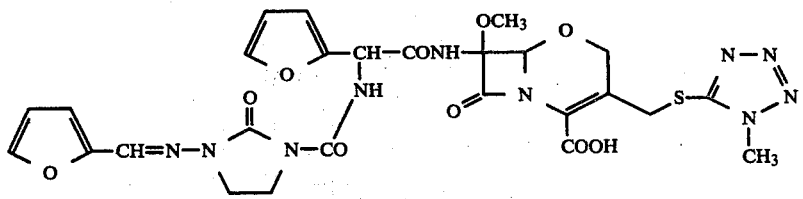

39 mg of the product obtained in Example 1 were dissolved in 0.4 ml of dichloromethane, and the solution was cooled to 0°. 0.4 ml of a 1:1 mixture of trifluoroacetic acid and anisole were then added, and the mixture was stirred for 25 minutes at this temperature. After the solvent had been distilled off on a rotary evaporator, the residue was diluted with benzene and the solution was concentrated again. After the residue had been dried in a high vacuum, it was triturated with ether, to which a few drops of dichloromethane had been added, and the product was filtered off under suction: 28 mg of a white powder.

$^1$H-NMR ppm inter alia DMF-d$_7$200 MHz: 3.36 and 3.50 (2s; 3H); 3.95 and 4.08 (1m and 1s, 7H); 4.38 (AB system, 2H); 4.68 (AB system, 2H) 5.18 (s, 1H); 6.00 and 6.03 (2d, 1H); 6.4–6.8 (m, 3H); 6.9–7.0 (m, 1H).

IR cm$^{-1}$ inter alia Nujol: 1785 s.

EXAMPLE 3

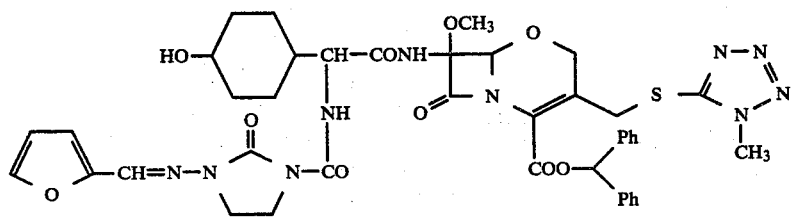

59 mg of 2-(2-oxo-3-furfurylideneamino-imidazolidin-1-yl)-carbonylaminopara-hydroxyphenylacetic acid were suspended in 0.5 ml of acetone, and a solution which had been prepared from 318 mg of N-methylmorpholine diluted to 10 ml with acetone was added. Thereafter, the mixture was cooled to −30° C., and 0.5 ml of a solution of 341 mg of ethyl chloroformate diluted to 10 ml with acetone was added, and the mixture was stirred for 1.5 hours at −25° C. A solution of 40 mg of diphenylmethyl 7-methoxy-7-amino-3-(1-methyl-1-tetrazol-5-ylthiomethyl)-1-oxadethia-3-cephem-4-carboxylate, dissolved in 0.5 ml of dimethylformamide, was then added, and the mixture was stirred for 1 hour at −25° C., for 3 hours at −20° C. and for 3 hours at −15° C. The working-up was effected by pouring the mixture into ice water, extracting (3 times) with chloroform, and washing the organic phase with water (once) and saturated sodium bicarbonate solution (twice), drying it and concentrating it in vacuo. It was possible to obtain the desired diphenylmethyl (DL-α-(2-oxo-3-furfurylideneamino-imidazolidin-1-yl)-carbonylaminoparahydroxyphenylacetamido)-3-(1-methyl-1-H-tetrazol-5-yl-thiomethyl)-1-oxadethia-3-cephem-4-carboxylate as a rigid foam by subsequent preparative thin-layer chromatography.

$^1$H-NMR ppm inter alia CDCl$_3$250 MHz: 3.52, 3.84 and 3.7–4.1 (2s and 1m, 10H); 4.2–4.7 (2m, 4H); 5.02 (s, 1H); 5.52 and 5.54 (2d, 1H); 6.5 (m, 1H); 7.80 (s, 1H); 9.10 and 9.14 (2d, 1H).

IR cm$^{-1}$ inter alia CHCl$_3$: 3150–3500 w, 3050–2800 w, 1785 s, 1740–1700 s, 1680 m, 1480 s, 1410 s, 1395 s, 1260 s.

EXAMPLE 4

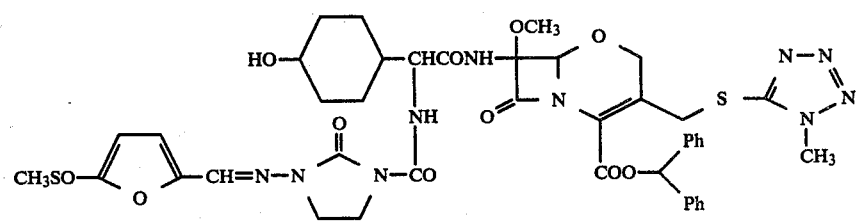

103 mg of 2-(2-oxo-3-(4-methylsulphinylfurfurylidene)-aminoimidazolidin-1-yl)-carbonylaminopara-hydroxyphenylacetic acid were suspended in 0.2 ml of dimethylformamide, and 0.1 ml of a solution of 1.3 ml of N-methylmorpholine in N,N-dimethylformamide, diluted to 5 ml, was added at room temperature. Thereafter, the mixture was cooled to −30°, and 0.1 ml of a solution of 1.28 g of ethyl chloroformate in dimethylformamide (total volume 5 ml) was added, and the mixture was stirred for 2.5 hours at −20° to −25°. A solution of 40 mg of diphenylmethyl 7-methoxy-7-amino-3-(1-methyl-1-H-tetrazol-5-yl-thiomethyl)-1-oxadethia-3-cephem-4-carboxylate dissolved in 0.45 ml of dimethylformamide was then added, and the mixture was stirred for 1 hour at −25°, for 1 hour at −18°, for 1.5 hours at −16° and overnight at −11°. The working-up was effected in the customary manner. It was possible to obtain the desired diphenylmethyl 7-methoxy-7-(DL-2--oxo-3(4-methylsulphinyl-furfurylidene)-amino-imidazolidin-1-yl)-carbonylamino-parahydroxyphenylacetamido)-3-(1-methyl-1-H-tetrazol-5-yl-thiomethyl)-1-oxadethia-3-cephem-4-carboxylate as a rigid foam by subsequent preparative thin-layer chromatography.

¹H-NMR ppm inter alia CD₃OD, DMSO-d₆250 MHz: 2.38 (2s, 3H); 3.22 and 3.40 (2s, 3H); 3.6–4.9 and 3.80 (m and s, 7H); 4.0 (2m, 4H); 5.00 (s, 1H); 5.40 and 5.42 (2s, 1H); 6.43 (m, 1H); 6.6–6.8 (m, 3H).

IR cm⁻¹ inter alia CHCl₃: 3400–3100 w, 3050–2800 m, 1785 s, 1720 s, 1670 s, 1510 m, 1480 s, 1390–1410 s, 1265 s.

EXAMPLE 5

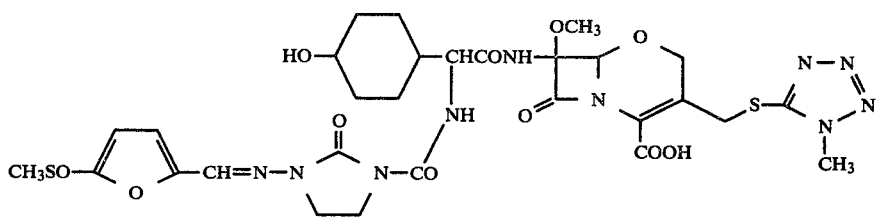

24 mg of the product obtained in Example 4 were dissolved in 0.4 ml of dichloromethane, and the solution was cooled to 0°. 0.4 ml of a 1:1 mixture of trifluoroacetic acid and anisole were then added, and the mixture was stirred for 25 minutes at this temperature. After the solvent had been distilled off on a rotary evaporator, the residue was diluted with benzene and the solution is concentrated again. After the residue had been dried in a high vacuum, it was triturated with ether, to which a few drops of dichloromethane had been added, and the solvent was evaporated off: 13 mg of a white powder.

¹H-NMR ppm inter alia DMF-d₇, 250 MHz: 258 (2s, 3H); 3.27 and 3.50 (2s, 3H); 3.96 (m, 4H); 4.09 and 4.10 (2s, 3H); 4.25–4.70 (2m, 4H); 5.18 (2s, 1H); 5.75 and 5.77 (2d, 1H); 6.7–6.9 (m, 4H), 9.04 and 9.24 (2d, 1H).

IR cm⁻¹ inter alia Nujol: 1780 s.

EXAMPLE 6

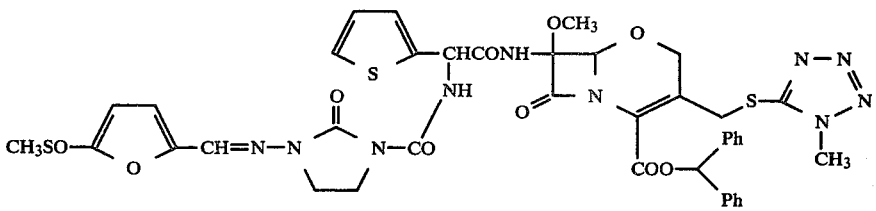

100 mg of 2-(2-oxo-3-(4-methylsulphinylfurfurylidene)-amino-imidazolidin-1-yl)-carbonylamino-thienylacetic acid were dissolved in 0.2 ml of N,N-dimethylformamide under a nitrogen atmosphere, and 26 µl of N-methylmorpholine were added at room temperature. Thereafter, the mixture was cooled to −30°, and 23 µl of ethyl chloroformate were added, and the mixture was then stirred for 3 hours at −20° to −25°. A solution of 40 mg of diphenylmethyl 7-methoxy-7-amino-3-(1-methyl-1-H-tetrazol-5-yl-thiomethyl)-1-oxadethia-3-cephem-4-carboxylate dissolved in 0.45 ml of dimethylformamide was then added, and the mixture was stirred for 1 hour at −20°, for 0.5 hour at −15°, for 1.5 hours at −13° and overnight at −10°. The working-up was effected in the customary manner. It was possible to obtain the desired diphenylmethyl 7-methoxy-7-(-DL-α2-oxo-3-(4-methylsulphinylfurfurylidene)-amino-imidazolidin-1-yl)-carbonylamino-thienylacetamido)-3-(1-methyl-1-H-tetrazol-5-yl-thiomethyl)-1-oxadethia-3-cephem-4-carboxylate as a rigid foam by subsequent preparative thin layer chromatography.

¹H-NMR ppm inter alia CDCl₃ 250 MHz: 2.46 (2s, 3H); 3.46 and 3.54 (2s, 3H); 3.6–3.8, 3.9–4.1, 3.84 and 3.85 (2m and 2s, 7H); 4.26 and 4.56 (2m, 4H); 5.04 and 5.08 (2s, 1H); 5.82 and 5.88 (2d, 1H); 9.00 and 9.08 (2d, 1H).

IR cm⁻¹ inter alia CHCl₃: 3500–3100 w, 3050–2800 w, 1785 s, 1715–1740 s, 1680 s, 1480 s, 1405 s, 1265 s.

EXAMPLE 7

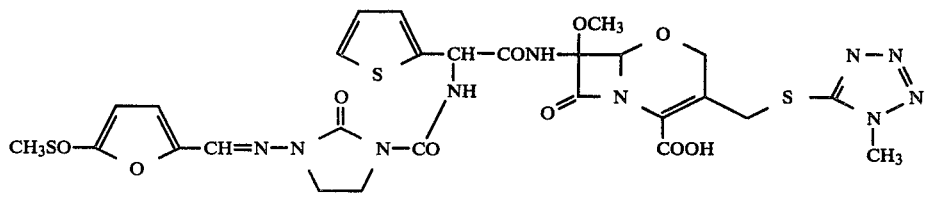

25 mg of the product obtained in Example 6 were dissolved in 0.4 ml of dichloromethane, and the solution was cooled to 0°. 0.4 ml of a 1:1 mixture of trifluoroacetic acid and anisole was then added, and the mixture was stirred for 25 minutes at this temperature. After the solvent had been distilled off on a rotary evaporator, the residue was diluted with benzene and the solution was concentrated again. After the residue had been dried in a high vacuum, it was triturated with ether, to which a few drops of dichloromethane had been added, and the product was filtered off under suction: 17 mg of a white powder.

$^1$H-NMR ppm inter alia DMF-d$_7$, 200 MHz: 2.51 (2s, 3H); 3.31 and 3.48 (2s, 3H); 3.91 (m, 4H); 4.03 (s, 3H); 4.34 and 4.60 (2m, 4H); 5.16 (s, 1H); 6.10 and 6.14 (2d, 1H); 7.38 (s, 1H); 9.13 and 9.08 (2d, 1H).

IR cm$^{-1}$ inter alia Nujol: 1785 s.

EXAMPLE 8

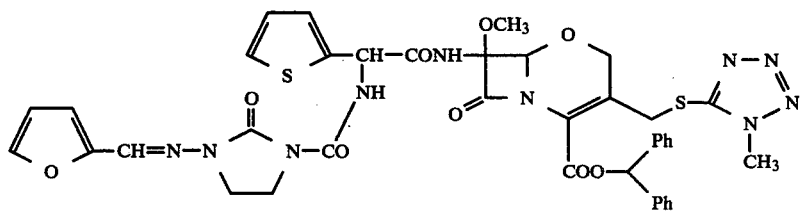

236 mg of 2-(2-oxo-3-furfurylideneamino-imidazolidin-1-yl)-carbonylamino-thienyl-acetic acid were suspended in 3 ml of absolute dichloromethane at room temperature, under a nitrogen atmosphere, and were dissolved by the addition of 86 μl of N-methylmorpholine. The mixture was cooled to −20° C., 56 μl of methanesulphonyl chloride were added dropwise, and the mixture was stirred for 1 hour at −20° C. Thereafter, the mixture was cooled to −30° C., and a solution of 254 mg of diphenylmethyl 7-methoxy-7-amino-3-(1-methyl-1-H-tetrazol-5-ylthiomethyl)-1-oxadethia-3-cephem-4-carboxylate and 60 μl of N-methylmorpholine in 4 ml of absolute dichloromethane was added. The mixture was allowed to warm slowly to 0° C., and was left to stand overnight at this temperature. The working-up was effected by pouring the mixture into 60 ml of saturated NaHCO$_3$ solution, extracting with dichloromethane (twice), and washing the organic phase with 60 ml of ice-cold 0.1 N HCl, saturated NaHCO$_3$ solution and water. After the organic phase had been dried over MgSO$_4$ and the solvent had been evaporated off in vacuo, an oil was obtained and was purified by chromatography on 25 g of silica gel (ethyl acetate). Yield: 73 mg of diphenylmethyl 7-methoxy-7-[D,L-(2-oxo-3-furfurylidene-amino-imidazolidin-1-yl)-carbonylamino-thienyl-acetamido]-3-(1-methyl-1-H-tetrazol-5-yl-thiomethyl)-1-oxadethia-3-cephem-4-carboxylate.

Rf: 0.31, 0.35 (ethyl acetate).

$^1$H-NMR (250 MHz, CDCl$_3$) δ=3.48, 3.56 (s. 3H, OCH$_3$), 3.86 (s, 3H, N—CH$_3$), 3.75, 3.95 (m, 4H, CH$_2$N), 4.30, 4.60 (m, 4H, CH$_2$S, CH$_2$O), 5.08, 5.11 (s, 1H, acetidinone—H), 5.86 (m, 1H,

—CH—D,L),
|

6.51 (M, 1H, furyl—H), 6.82 (M, 1H, furyl—H), 6.92 (s, 1H, CHPh$_2$), 7.0, 7.08 (m, 2H, thienyl—H), 7.2–7.6 (m, 13H, H aromatic, -heteroaromatic, —CH=N—), 7.78, 7.80 (s, 1H, CONH), 9.08, 9.15 (d, J=Hz, 1H, CH—NHCO).

IR (KBr): 3286 (NH amide), 1784 (C=O, β-lactam), 1725 (C=O, ester), 1668, 1650 cm$^{-1}$ (C=O, amide semicarbazide; C=N).

EXAMPLE 9

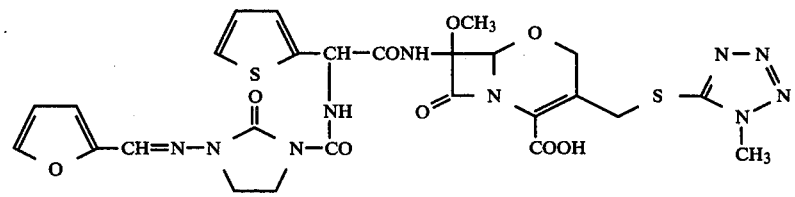

60 mg of the product obtained in Example 8 were dissolved in 1.2 ml of dichloromethane, and the solution was cooled to 0°. 1.0 ml of a 1:1 mixture of trifluoroacetic acid and anisole were then added, and the mixture was stirred for 25 minutes at this temperature. After the solvent had been distilled off on a rotary evaporator, the residue was diluted with benzene and the solution was concentrated again. After the residue had been dried in a high vaccum, it was triturated with ether, to which a few drops of dichloromethane had been added, and the product was filtered off under suction: 47 mg of a white powder.

Melting point: 165°–167° C. (decomposition).

$^1$H-NMR (250 MHz, DMSO) δ=3.40, 3.42 (s, 3H, OCH$_3$), 3.95 (s, 3H, N—CH$_3$), 3.8 (m, 4H, CH$_2$N), 4.23, 4.5 (m, 4H, CH$_2$S, CH$_2$O), 5.13 (s, 1H, acetidinone—H), 5.75, 5.92 (m, 1H,

—CH—D,L),
|

6.65 (m, 1H, furyl—H), 6.89 (d, J=4.5 Hz, 1H, fury-1—H), 6.9–7.6 (m, 4H), thienyl—H, furyl—H), 7.77 (s, 1H, CH=N), 7.97 (s, 1H, NH), 9.0 (m, 1H, NH).

IR (KBr): 3400–3300 (b, OH), 1779 (C=O, β-lactam), 1724 (C=O, acid), 1678 (C=O, amide, semicarbazide; C=N).

EXAMPLE 10

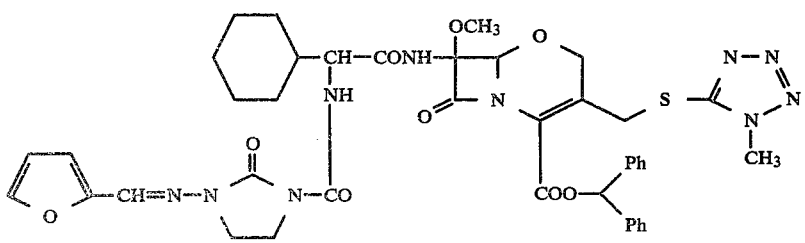

463 mg of 2-(2-oxo-3-furfurylideneamino-imidazolidin-1-yl)-carbonylamino-phenylacetic acid were suspended in 3 ml of absolute dichloromethane at room temperature, under a nitrogen atmosphere, and were dissolved by the addition of 172 μl of N-methylmorpholine. The mixture was cooled to −30° C., 241 μl of trifluoromethanesulphonic acid anhydride were added dropwise, and the mixture was stirred for 1 hour at −30° C. A solution of 509 mg of diphenylmethyl 7-methoxy-7-amino-3-(1-methyl-1-H-tetrazol-5-ylthiomethyl)-1-oxadethia-3-cephem-4-carboxylate and 121 μl of N-methylmorpholine in 5 ml of absolute dimethylformamide was added to the mixture. The mixture was allowed to warm slowly to 0° C., and remained standing overnight at this temperature. The working-up was effected by pouring the mixture into 100 ml of saturated NaHCO₃ solution, extracting with dichloromethane (3 times), and washing the organic phase with 100 ml of ice-cold 0.1 N HCl, saturated NaHCO₃ solution and water. After the organic phase had been dried over MgSO₄ and the solvent had been evaporated off in vacuo, the crude product was chromatographed on 65 g of silica gel (ethyl acetate). Yield: 183 mg of diphenylmethyl 7-methoxy-7-[D,L-(2-oxo-3-furfurylideneaminoimidazolidin-1-yl)-carbonylaminophenylacetamido]-3-(1-methyl-1-H-tetrazol-5-yl-thiomethyl)-1-oxadethia-3-cephem-4-carboxylate.

Rf: 0.26 (ethyl acetate).

$^1$H-NMR (250 MHz, CDCl₃) δ=3.28, 3.50 (s, 3H, OCH₃), 3.84 (s, 3H, N—CH₃), 3.5–4.0 (m, 4H, CH₂N), 4.25, 4.5 (m, 4H, CH₂S, CH₂O), 5.01, 5.09 (s, 1H, acetidinone—H), 5.64, 5.75 (d, J=7 Hz,

D,L-CH—),
|

6.48 (m, 1H, furyl—H), 6.80 (m, 1H, furyl—H), 6.90 (s, 1H, CHPh₂), 7.2–7.6 (m, 18H), 9.16, 9.28 (d, J=7 Hz, 1H, CHNHCO).

IR (KBr)=3394 (NH amide), 1787 (C=O, β-lactam), 1732 (C=O, acid), 1681 cm$^{-1}$ (C=O, amide; C=O, C=N, semicarbazide).

EXAMPLE 11

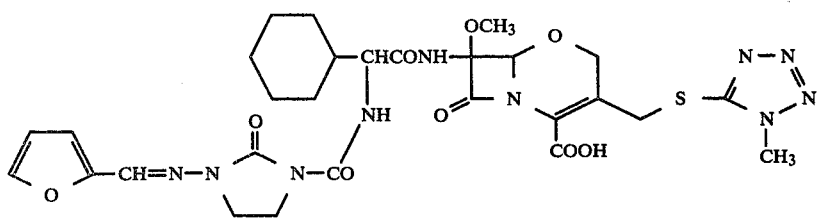

196 mg of the product obtained in Example 10 were dissolved in 3 ml of dichloromethane, and the solution was cooled to 0°. 2.4 ml of a 1:1 mixture of trifluoroacetic acid and anisole were then added, and the mixture was stirred for 25 minutes at this temperature. After the solvent had been distilled off on a rotary evaporator, the residue was diluted with benzene and the solution was concentrated again. After the residue had been dried in a high vacuum, it was triturated with ether, to which a few drops of dichloromethane had been added, and the product was filtered off under suction: 153 mg of a white powder.

Melting point: 142° C. agglomeration, 167° C. (decomposition).

Rf: 0.15 (BABA)

$^1$H-NMR (250 MHz, DMSO) δ=3.06, 3.38 (s, 3H, OCH₃), 3.45, 3.8 (m, 4H, NCH₂), 4.15–4.55 (m, 4H, CH₂S, CH₂O), 5.08, 5.11 (s, 1H, acetidinone—H), 5.66 (d, J=9 Hz, 1H, NHCHCO), 6.65 (m, 1H, furyl—H), 6.87 (d, J=4.5 Hz, furyl—H), 7.0–7.5 (m, 6H, Ph, furyl—H), 7.78 (s, 1H, CH=N), 7.86 (s, 1H, NH), 8.98, 9.13 (d, J=9 Hz, 1H, NH).

IR (KBr): 3480 (b, OH), 1783 (C=O, β-lactam), 1728 (C=O, ester), 1680, 1640 [sh] (C=O, amide, semicarbazide; C=N).

EXAMPLE 12

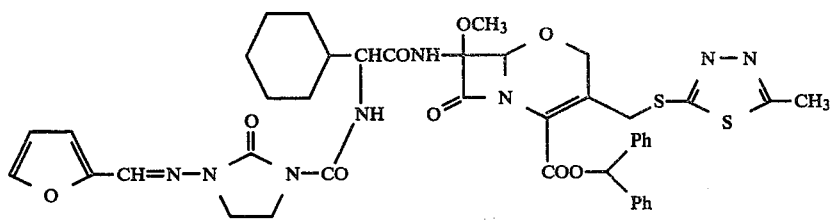

632 mg of 2-(2-oxo-3-furfurylideneamino-imidazolidin-1-yl)-carbonylamino-phenylacetic acid were suspended in 4 ml of absolute dichloromethane at room temperature, under a nitrogen atmosphere, and were dissolved by the addition of 234 μl of N-methylmorpholine. The mixture was cooled to −30° C., 328 μl of trifluoromethanesulphonic acid anhydride were added dropwise, and the mixture was stirred for 45 minutes at −30° C. A solution of 716 mg of diphenylmethyl 7-methoxy-7-amino-3-(2-methyl-1-thia-3,4-diazol-5-ylthiomethyl)-1-oxadethia-3-cephem-4-carboxylate and 165 μl of N-methylmorpholine in 10 ml of absolute dichloromethane was added to the mixture. The mixture was allowed to warm slowly to 0° C., and remained standing overnight at this temperature. The working-up was effected by pouring the mixture into 150 ml of saturated NaHCO₃ solution, extracting with dichloromethane (3 times), and washing the organic phase with 150 ml of ice-cold 0.1 N HCl, saturated NaHCO₃ solution and water. After the organic phase had been dried over MgSO₄ and the solvent had been evaporated off in vacuo, the crude product was chromatographed on 100 g of silica gel (ethyl acetate). Yield: 295 mg of diphenylmethyl 7-methoxy-7-[D,L-(2-oxo-3-furfurylideneaminoimidazolidin-1-yl)-carbonylaminophenylacetamido]-3-(2-methyl-1-thia-3,4-diazol-5-ylthiomethyl)-1-oxadethia-3-cephem-4-carboxylate.

Rf: 0.25 (ethyl acetate).
Melting point: 158° C.
¹H-NMR (200 MHz, CDCl₃) δ=2.69, 2.72 (s, 3H, CH₃), 3.30, 3.53 (s, 3H, OCH₃), 3.7–4.6 (m, 8H, CH₂N, CH₂S, CH₂O), 5.03, 5.08 (s, 1H, acetidinone—H), 5.60, 5.66 (d, J=7.5 Hz, 1H, NHCHCO), 6.50 (m, 1H, furyl—H), 6.82 (m, 1H, furyl—H), 6.90 (s, 1H, CHPh₂), 7.0 (s, 1H NH), 7.25–7.6 (m, 16H, Ph, furyl—H), 7.74–7.76 (s, 1H, CH=N), 9.16, 9.24 (d, J=7.5 Hz, 1H, NH).

IR (KBr): 3303 (NH amide), 1784 (C=O, β-lactam), 1726 (C=O, ester), 1679 cm⁻¹ (C=O, amide; C=O, C=N semicarbazide).

EXAMPLE 13

843 mg of 2-(2-oxo-3-furfurylideneamino-imidazolidin-1-yl)-carbonylamino-phenylacetic acid were suspended in 5 ml of absolute dichloromethane at room temperature, under a nitrogen atmosphere, and were dissolved by the addition of 309 μl of N-methylmorpholine. The mixture was cooled to −30° C., 433 μl of trifluoromethanesulphonic acid anhydride were added dropwise, and the mixture was stirred for 45 minutes at −30° C. A solution of 919 mg of diphenylmethyl 7-methoxy-7-amino-3-(1-thia-3,4-diazol-2-ylthiomethyl)-1-oxadethia-3-cephem-4-carboxylate and 218 μl of N-methylmorpholine in 12 ml of absolute dichloromethane was added to the mixture. The mixture was allowed to warm slowly to 0° C., and remained standing overnight at this temperature. The working-up was effected by pouring the mixture into 200 ml of saturated NaHCO₃ solution, extracting with dichloromethane (3 times), and washing the organic phase with 200 ml of ice-cold 0.1 HCl, saturated NaHCO₃ solution and water. After the organic phase had been dried over magnesium sulphate and the solvent had been evaporated off in vacuo, the crude product was chromatographed on 140 g of silica gel (ethyl acetate). Yield: 153 mg of diphenylmethyl 7-methoxy-7-[D,L-(2-oxo-3-furfurylideneaminoimidazolidin-1-yl)-carbonylaminophenylacetamido]-3-(1-thia-3,4-diazol-2-ylthiomethyl)-1-oxadethia-3-cephem-4-carboxylate.

RF: 0.25 (ethyl acetate).
Melting point: 164° C.³
¹H-NMR (250 MHz, CDCl₃) δ=3.28, 3.54 (s, 3H, OCH₃), 3.7, 3.9 (m, 4H, CH₂N), 4.2–4.55 (m, 4H, CH₂S, CH₂O), 5.06, 5.10 (s, 1H, acetidinone—H), 5.63, 5.71 (d, J=7 Hz, 1H, NHCHCO), 6.51 (m, 1H, furyl—H), 6.82 (d, J=4.5 Hz, 1H, furyl—H), 7.1–7.6 (m, 17H, Ph, furyl—H, NH), 7.69, 773 (s, 1H, CH=N), 9.0, 9.04 (s, 1H, thiadiazole—H), 9.19, 9.28 (d, J=7 Hz, 1H, NH).

IR (KBr): 3299 (NH, amide), 1787 (C=O, β-lactam), 1724 (C=O, ester), 1673 cm⁻¹ (C=O, amide, semicarbazide; C=N).

EXAMPLE 14

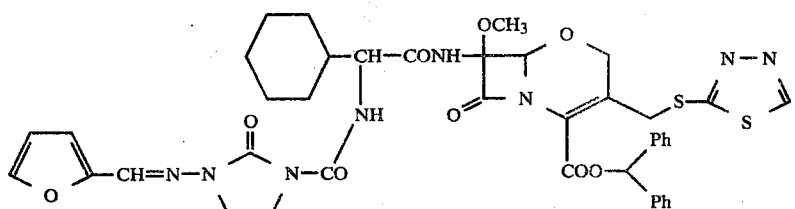

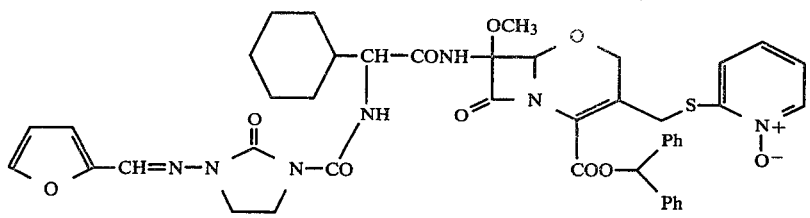

53 mg of 2-(2-oxo-3-furfurylideneamino-imidazolidin-1-yl)carbonylamino-phenylacetic acid were suspended in 0.3 ml of absolute dichloromethane at room temperature, under a nitrogen atmosphere, and were dissolved by the addition of 20 μl of N-methylmorpholine. The mixture was cooled to −30° C., 27 μl of trifluoromethanesulphonic acid anhydride were added dropwise, and the mixture was stirred for 1 hour at −30° C. A solution of diphenylmethyl 7-methoxy-7-amino-3-(1-oxopyrid-2-yl-thiomethyl)-1-oxadethia-3-cephem-4-carboxylate and 14 μl of N-methylmorpholine in 1.5 ml of absolute dichloromethane was added to the mixture. The mixture was allowed to warm slowly to 0° C., and remained standing overnight at this temperature. The working-up was effected by pouring the mixture into 60 ml of ice-cold 1 N HCl, extracting with dichloromethane (twice), and washing the organic phase with saturated NaHCO$_3$ solution and water. After the organic phase had been dried over MgSO$_4$ and the solvent had been evaporated off in vacuo, the crude product was purified by chromatography on 10 g of silica gel (acetone:ethyl acetate=7:3). Yield: 39 mg of diphenylmethyl 7-methoxy-7-[(2-oxo-3-furfurylidene-amino-imidazolidin-1-yl)-carbonylamino-phenylacetamido]-3-(1-oxopyrid-2-yl-thiomethyl)-1-oxa-dethia-3-cephem-4-carboxylate.

Rf: 0.58 (BABA).

Melting point: 178° C. (decomposition).

$^1$H-NMR (250 MHz, CDCl$_3$) δ=3.54 (s, 3H, OCH$_3$), 3.8–4.4 (m, 8H, CH$_2$N, CH$_2$S, CH$_2$O), 5.04 (s, 1H, acetidinone—H), 5.27 (d, J=8 Hz, 1H, NHCHCO), 6.50 (m, 1H, furyl—H), 6.81 (d, J=4.5 Hz, 1H, furyl—H), 7.05–7.55 (m, 20H, Ph, NY, pyridyl—H, furyl—H), 7.80 (s, 1H, CH═N), 8.25 (m, 1H, pyridyl—H), 9.13 (d, J=8 Hz, 1H NHCHCO).

IR (KBr): 3928 (NH, amide), 1786 (C═O, β-lactam), 1726 (C═O, ester), 1678 (C═O, amide, ureido; C═N).

EXAMPLE 15

1.15 g of 2-(2-oxo-3-furfurylideneamino-imidazolidin-1-yl)-carbonylaminophenylacetic acid were suspended in 6 ml of absolute dichloromethane at room temperature, under a nitrogen atmosphere, and were dissolved by the addition of 0.43 ml of N-methylmorpholine. The mixture was cooled to −30° C., 0.6 ml of trifluoromethanesulphonic acid anhydride were added, and the mixture was stirred for 45 minutes at −30° C. A freshly prepared solution of 1.07 g of diphenylmethyl 7-methoxy-7-amino-3-chloromethyl-1-oxadethia-3-cephem-4-carboxylate and 0.3 ml of N-methylmorpholine in 15 ml of absolute dichloromethane were added. The mixture was allowed to warm to 0° C. and remained standing overnight at this temperature. The working-up was effected by pouring the mixture into 200 ml of saturated NaHCO$_3$ solution, extracting with dichloromethane (twice), and washing the organic phase with 200 ml of ice-cold 0.1 N HCl, saturated NaHCO$_3$ solution and water. After the organic phase had been dried over magnesium sulphate, the crude product was chromatographed on 150 g of silica gel and then on 40 g of silica gel (toluene/ethyl acetate 1:3). Diphenylmethyl 7-methoxy-7-[D,L-(2-oxo-3-furfurylideneaminoimidazolidin-1-yl)-carbonylamino-phenylacetamido]-3-chloromethyl-1-oxa-dethia-3-cephem-4-carboxylate was obtained.

Rf: 0.31 (toluene:ethyl acetate 1:3).

Melting point: 184° C.

$^1$H-NMR (250 MHz, CDCl$_3$) δ=3.5. 3.7 (s, 3H, OCH$_3$), 3.3–4.5 (m, 8H, CH$_2$N, CH$_2$S, CH$_2$O), 5.5 (d, J=8.5 Hz, 1H, NHCHCO), 6.5 (m, 1H, furyl—H), 6.8 (m, 1H, furyl—H), 7.0–7.6 (m,), 7.8 (s, 1H, CH═N), 9.2 (m, 1H, NH).

IR (KBr): 3300 (NH, amide), 1785 (C═O, β-lactam), 1727 (C═O, ester), 1784 (C═O, amide, semicarbazide; C═N).

EXAMPLE 16

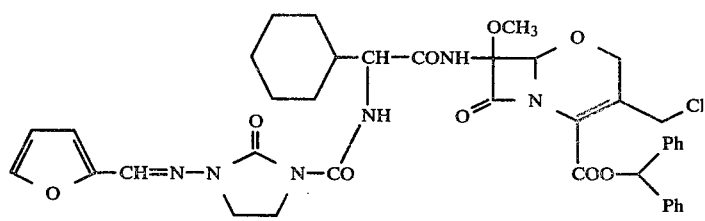

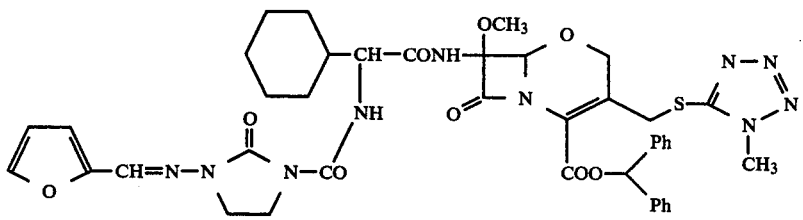

553 mg of 2-(2-oxo-3-furfurylideneamino-imidazolidin-1-yl)-carbonylamino-phenylacetic acid were suspended in 3.2 ml of absolute dichloromethane at room temperature, under a nitrogen atmosphere, and were dissolved by the addition of 205 μl of N-methylmorpholine. The mixture was cooled to −30° C., 287 μl of trifluoromethanesulphonic acid anhydride were added, and the mixture was stirred for 45 minutes at −30° C. A solution of 571 mg of diphenylmethyl 7-amino-3-(1-methyl-1-H-tetrazol-5-ylthiomethyl)-1-oxadethia-3-cephem-4-carboxylate and 144 μl of N-methylmorpholine in 8 ml of absolute dichloromethane was added, and the mixture was stirred for 3 hours at −20° C. The working-up was effected by pouring the mixture into 100 ml of saturated NaHCO₃ solution, extracting with dichloromethane (3 times), and washing the organic phase with cold 0.1 N HCl, saturated NaHCO₃ solution and water. After the organic phase had been dried over magnesium sulphate and the solvent had been evaporated off in vacuo, the crude product was chromatographed on 60 g of silica gel (ethyl acetate). Yield: 204 mg of diphenylmethyl 7-[(2-oxo-3-furfurylideneaminoimidazolidin-1-yl)-carbonylamino-phenylacetamido]-3-(1-methyl-1-H-tetrazol-5-yl-thiomethyl)-1-oxadethia-3-cephem-4-carboxylate.

Rf: 0.30 (ethyl acetate).
Melting point: 172° C.

¹H-NMR (200 MHz, CDCl₃) δ=3.5–4.0 (m, 4H, CH₂N), 3.83 (s, 3H, NCH₃), 4.18, 4.33 (d, J=14 Hz, 2H, CH₂O), 4.54, 4.65 (d, J=18 Hz, 2H, CH₂S), 4.70 (dd, J=1 Hz, J=7.5 Hz, 1H, acetidinone—H), 5.0 (d, J=1 Hz, 1H, acetidinone—H), 5.59 (d, J=7.5 Hz, 1H, NHCHCO), 6.50 (m, 1H, furyl—H) 6.81 (d, J=4.5 Hz, 1H, furyl—H), 6.94 (s, 1H, CHPh₂), 7.2–7.6 (m, 16H, pH, furyl—H), 7.70 (s, 1H, CH=N), 9.25 (d, J=7.5 Hz, 1H, NH).

IR (KBr): 3310 (NH, amide), 1789 (C=O, β-lactam), 1732 (C=O, ester), 1679 cm⁻¹ (C=O, amide, semicarbazide; C=N).

EXAMPLE 17

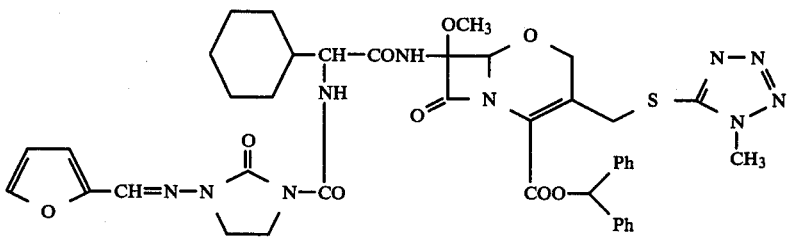

98 mg of diphenylmethyl 7-[(2-oxo-3-furfurylideneaminoimidazolidin-1-yl)-carbonylamino-phenylacetamido]-3-(1-methyl-1-H-tetrazol-5-ylthiomethyl)-1-oxadethia-3-cephem-4-carboxylate were dissolved in 0.8 ml of absolute dichloromethane, under a nitrogen atmosphere, and the solution was cooled to −70° C. 15 μl (0.22 mmol, 1.8 equivalents—iodometrically determined) of freshly prepared t-butyl hypochlorite and immediately thereafter, in the course of 30 seconds, 90 μl (0.18 mmol, 1.5 equivalents) of a freshly prepared 2 M solution of lithium methoxide in anhydrous methanol were added dropwise. The mixture was then stirred for 12.0 minutes at −70° C., 0.1 ml of glacial acetic acid were then added rapidly, and the mixture stirred for a further 2 minutes at −70° C. The reaction mixture was worked up by pouring it into 100 ml of ice-cold 0.1 N Na₂S₂O₃ solution, while stirring, and extracting the mixture with 3 times 50 ml of dichloromethane. The organic extracts were washed with twice 80 ml of cold saturated NaHCO₃ solution and with water, and were dried over magnesium sulphate. After the solvent had been evaporated off in vacuo, 92 mg of diphenylmethyl 7-methoxy-[(2-oxo-3-furfurylidene-aminoimidazolidin-1-yl)-carbonylamino-phenylacetamido]-3-(1-methyl-1-H-tetrazol-5-yl-thiomethyl)-1-oxa-dethia-3-cephem-4-carboxylate were obtained by triturating the residue with ether.

Melting point from 145° C. (decomposition).
Rf: 0.26 (ethyl acetate)
IR (KBr): 1788, 1730, 1682 cm⁻¹.

EXAMPLE 18

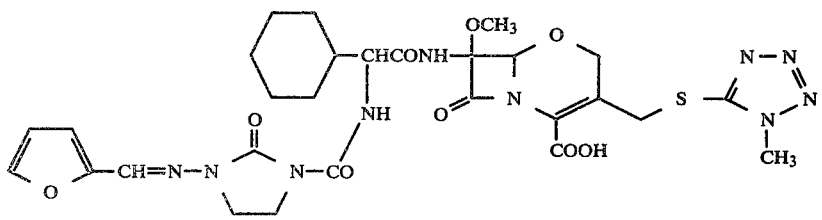

100 mg of 7-methoxy-7-phenylglycylamino-3-(1-methyl-1-H-tetrazol-5-ylthiomethyl)-1-oxadethia-3-cephem-4-carboxylic acid trifluoroacetate were dissolved in 80% strength aqueous tetrahydrofuran, and reacted with 41 mg of 1-chlorocarbonyl-2-oxo-3-furylideneaminoimidazole at constant pH (7.2) and with cooling. Thereafter, the mixture was diluted with water, extracted twice by shaking with ethyl acetate, covered with a layer of fresh ethyl acetate and acidified to pH 1.8, and extracted again with ethyl acetate. Drying and concentrating the ethyl acetate phases gave 7-methoxy-7-[D,L-(2-oxo-3-furfurylidene-amino-imidazolidin-1-yl)-carbonylamino-phenylacetamido]-3-(1-methyl-1-H-tetrazol-5-yl-thiomethyl)-1-oxadethia-3-cephem-4-carboxylic acid (see Example 11).

The present invention also comprises pharmaceutically acceptable bioprecursors of the active compounds of the present invention.

For the purposes of this specification the term "pharmaceutically acceptable bioprecursor" of an active compound of the invention means a compound having a structural formula different from the active compound but which nonetheless, upon administration to an animal or human being, is converted in the patient's body to the active compound.

EXAMPLE 19 imidazolidin-1-yl)-carbonylamino-phenyl acetic acid after 12 hours at 0° C. and chromatography (ethyl acetate:toluene 95:5) 50 mg of the corresponding oxacephem as a colorless hard foam.

$^1$H-NMR (250 MHz, CDCl$_3$-DMSO)$\delta$3.72–3.85 (m, 4H, CH$_2$N), 4.01 (s, 3H, NCH$_3$), 4.22, 4.30 (AB-Signal, J=14 Hz, CH$_2$S), 4.59, 4.72 (AB-signal, J=18 Hz), 5.01 (d, J=4 Hz, 1H, H-6), 5.54 (dd, J=4 Hz, J=9 Hz, 1H, H-7), 5.66 (d, J=7, 5 Hz, NHCHCO), 6.50, 6.81 (m, 2H, furyl—H), 6.99 (s, 1H, CHPh$_2$), 7.25–7.75 (m, 17H, C$_6$H$_5$, furyl—H, CH=N), 8.40 (d, J=9 Hz, 1H, NH) 9.16 (d, J=7.5 Hz, 1H, CHNHCO).

EXAMPLE 20

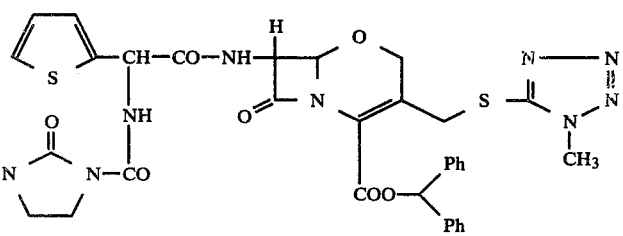

As described in Example 6, one obtains from 290 mg 7-amino-3-(1-methyl-1-H-tetrazol-5-yl-thiomethyl)-1-oxadethia-3-cephem-4-carboxylic acid diphenyl methyl ester and 724 mg 2-[2-oxo-3-(4-methylsulphinylfur-furylidene)-amino-imidazolidin-1-yl]-carbonylamino-thienyl acetic acid after 4 hours at −20° C. 312 mg of the corresponding oxacephem.

$^1$H-NMR (250 MHz, CDCl$_3$)$\delta$2.45 (s, 3H, CH$_3$SO—), 3.7–4.0 (m, CH$_2$N), 3.83 (s, NCH$_3$) zus. 7H, 4.25 (m, 2H, CH$_2$S), 4.57 (m, 2H, CH$_2$O), 5.03 (d, J=4 Hz, 1H, H-6), 5.55 (dd, J=4 Hz, J=8.5 Hz, 1H, H-7), 5.82 (d, J=7.5 Hz, 1H, NHCHCO), 6.40 (d, J=4 Hz, 1H), 6.8–7.7 (m, 17H, furyl—H, thienyl—H, CH=N, C$_6$H$_5$, NH), 9.03

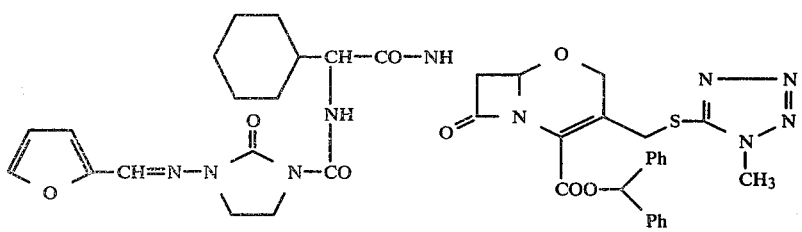

As described in Example 10 one obtains from 90 mg 7-amino-3-(1-methyl-1-H-tetrazol-5-yl-thiomethyl)-1-oxadethia-3-cephem-4-carboxylic acid diphenyl methyl ester and 87 mg 2-(2-oxo-3-furfurylideneamino- (d, J=7.5 Hz, 1H, CHNHCO).

EXAMPLE 21

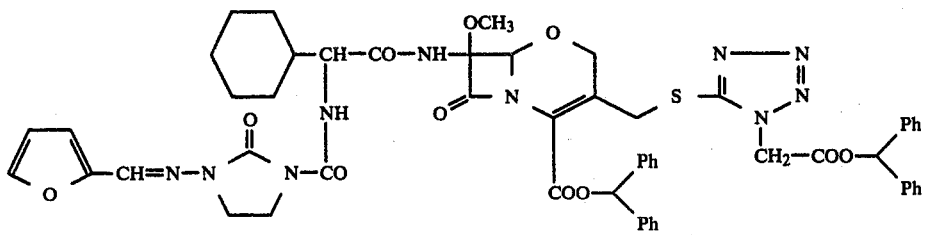

As described in Example 10, one obtains from 1.34 g 7-amino-7-methoxy-3-(1-carboxymethyl-1-H-tetrazol-5-yl-thiomethyl)-1-oxadethia-3-cephem-4 carboxylic acid-bis-diphenyl methyl ester and 0.87 g 2-(2-oxo-3-furfurylidenamino-imidazolidin-1-yl)-carbonyl-amino-phenyl acetic acid 0.53 g of the corresponding oxacephem as a hard foam.

Rf=0.35 (toluene:ethylacetate 6:4).

$^1$H-NMR (250 MHz, CDCl$_3$)δ3.38, 3.53 (s, 3H, OCH$_3$), 3.84, 3.86 (s, 3H, NCH$_3$), 3.5–4.0 (m, CH$_2$N), 3.7–4.1 (m, 4H, CH$_2$N), 4.24 (t, J=6 Hz, CH$_2$N), 4.27 (m, CH$_2$S) zus. 4H, 4.60, 4.81 (AB-signal, J=18 Hz, 2H, CH$_2$O), 4.89, 5.05 (s, 1H, azetidinon—H), 5.66, 5.72 (d, J=7 Hz, 1H, NHCHCO), 6.49, 6.82 (m, 2H, furyl—H), 6.95 (s, 1H, CHPh$_2$), 7.2–7.6 (m, 18H, C$_6$H$_6$, NH, CH=N, furyl—H), 9.17, 9.29 (d, J=7 Hz, CHNHCO).

IR (KBr) 1789 (C=O, β-lactam), 1714 (C=O, ester), 1679 cm$^{-1}$ (C=O, amide; C=N).

EXAMPLE 23

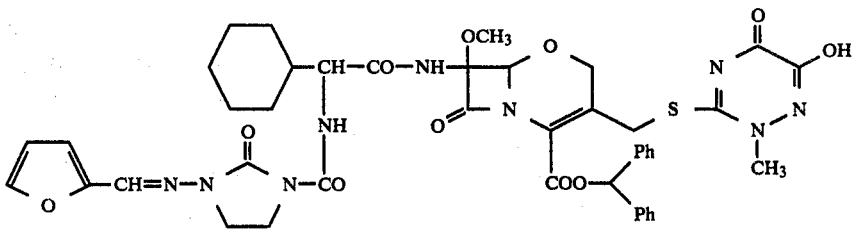

As described in Example 10, one obtains from 387 mg 7-amino-7-methoxy-3-(1-methyl-5-hydroxy-4-oxo-1,4-dihydro-1,3,6-triazin-2-yl)-thiomethyl-1-oxadethia-3-cephem-4-carboxylic acid diphenyl methyl ester and 325 mg 2-(2-oxo-3-furfurylideneamino-imidazolidin-1-yl)-carbonylamino-phenyl acetic acid 213 mg of the corresponding oxacephem as a powder.

Rf=0.3 (BABA).

$^1$H-NMR (250 MHz, DMSO)δ3.34, 3.48, 3.53 (s, 6H, OCH$_3$, NCH$_3$), 3.6–4.3 (m, 6H, CH$_2$N, CH$_2$S), 4.55 (m, 4.2 (m, 2H, CH$_2$S), 4.53, 4.70 (AB-Signal, J=19 Hz, 2H, CH$_2$O), 4.85, 4.80 (s, 1H, acetidinon—H), 5.07 (s, 2H, N—CH$_2$—COO), 5.63, 5.71 (d, J=7.5 Hz, 1H, NHCHCO), 6.48, 6.81 (m, 2H, furyl—H), 6.92 (s, 1H, CHPh$_2$), 7.2–7.6 (m, 28H, C$_6$H$_5$, NH, CH=N, furyl—H)m 9.11, 9.18 (d, J=7.5 Hz, 1H, CHNHCO).

IR (KBr) 1778 (C=O, β-lactam), 1750 (C=O, ester), 1717 (C=O, ester), 1676 cm$^{-1}$ (C=O, amide; C=N).

EXAMPLE 22

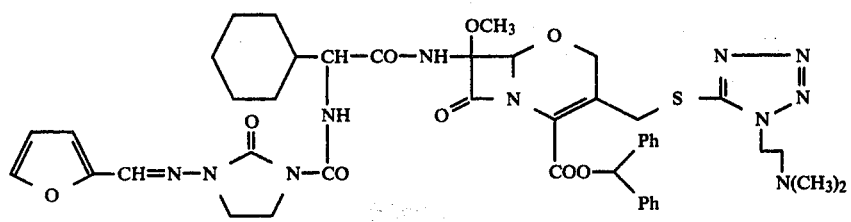

As described in Example 10, one obtains from 737 mg 7-amino-7-methoxy-3-(1-dimethylaminoethyl)-1-H-tetrazol-5-yl-thiomethyl)-1-oxadethia-3-cephem-4-carboxylic acid diphenyl methyl ester and 604 mg 2-(2-oxo-3-furfurylidenamino-imidazolidin-1-yl)-carbonylaminophenyl acetic acid after chromatography (ethyl acetate: acetone) and treating with chloroform/ethyl acetate 235 mg of the corresponding oxacephem as a powder.

$^1$H-NMR (250 MHz, CDCl$_3$)δ2.23 (s, 6H, N(CH$_3$)$_2$), 2.70 (t, J=6 Hz, 2H, CH$_2$N), 3.32, 3.55 (s, 3H, OCH$_3$), 2H, CH$_2$O), 5.16, 5.24 (s, 1H, H-6), 5.67, 5.69 (d, J=7.5 Hz, 1H, NHCHCO), 6.5, 6.8 (m, 2H, furyl—H), 7.00 (s, 1H, CHPh$_2$), 7.2–7.7 (m, 18H, C$_6$H$_5$, NH, CH=N, furyl—H), 9.14, 9.20 (d, J=7.5 Hz, CHNHCO), 9.41 (6s, 1H, OH).

IR (KBr) 3400 (OH), 1785 (C=O, β-lactam), 1727 (C=O, ester), 1680 (C=O, amide; C=N).

EXAMPLE 24

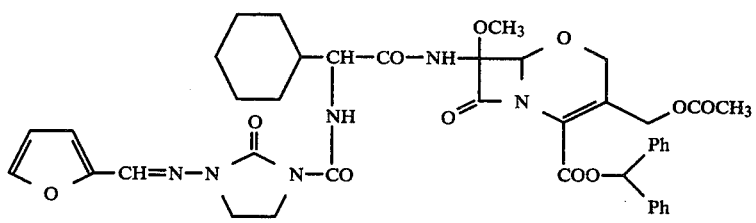

As described in Example 10, there were obtained from 2.13 g 3-acetoxymethyl-7-amino-7-methoxy-1-oxadethia-3-cephem-4-carboxylic acid diphenyl methyl ester and 2.18 g 2-(2-oxo-3-furfurylideneamino-imidazolidin-1-yl)-carbonylamino-phenyl acetic acid and chromatography of the crude product (toluene-:ethyl acetate 1:4) 1.67 g of the corresponding oxacephem as a light hard foam.

$^1$H-NMR (250 MHz, CDCl$_3$)δ1.98, 2.05 (s, 3H, OCOCH$_3$), 3.29, 3.48 (s, 3H, OCH$_3$), 3.5–4.0 (m, 4H, CH$_2$N), 4.4–4.8 (m, 4H, CH$_2$O), 5.01, 5.06 (s, 1H, H-6), 5.65, 5.76 (d, J=7 Hz, 1H, NHCHCO), 6.47, 6.79 (m, 2H, furyl—H), 6.92 (s, 1H, CHPh$_2$), 7.2–7.7 (m, 18H, C$_6$H$_5$, NH, CH=N, furyl—H), 9.15, 9.27 (d, 1H, CHNHCO).

IR (KBr) 3299 (NH), 1784 (C=O, β-lactam), 1720, 1730 (C=O, ester), 1677 (C=O, amide; C=N).

EXAMPLE 25

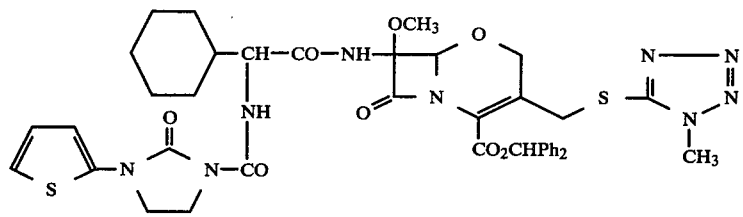

As described in Example 10, there were obtained from 1.53 g 7-amino-7-methoxy-3-(1-methyl-1-H-tetrazol-5-yl-thiomethyl)-1-oxadethia-3-cephem-4-carboxylic acid diphenyl methyl ester and 1.35 g 2-[2-oxo-3-(2-thienyl)-imidazolidin-1-yl]-carbonylaminophenyl acetic acid after chromatography (ethyl acetate:toluene 57:43) 1.57 g 7-methoxy-7-{D, L-[2-oxo-3-(2-thienyl)-imidazolidin-1-yl]-carbonylamino-phenylacetamido}-3-(1-methyl-1-H-tetrazol-5-yl-thiomethyl)-1-oxadethia-3-cephem-4-carboxylic acid diphenyl methyl ester.

Mp. 162° C. (Decomp.),
Rf=0.22 (ethyl acetate:toluene 1:1).

$^1$H-NMR (250 MHz, CDCl$_3$)δ3.31, 3.52 (s, 3H, OCH$_3$), 3.82, 3.84 (s, 3H, NCH$_3$), 3.7–4.1 (m, 4H, CH$_2$N), 4.2–4.6 (m, 4H, CH$_2$S, CH$_2$O), 5.03, 5.09 (s, 1H, azitidinon—H), 5.65, 5.83 (d, J=7 Hz, 1H, NHCHCO), 6.45 (m, 1H, thienyl—H), 6.8–7.6 (m, 19H, Ph, thienyl—H, CHPh$_2$, NH), 9.07, 9.17 (d, J=7 Hz, 1H, CHNHCO).

IR (KBr) 1787 (C=O, β-lactam), 1711 (C=O, ester), 1680 cm$^{-1}$ (C=O, amide).

EXAMPLE 26

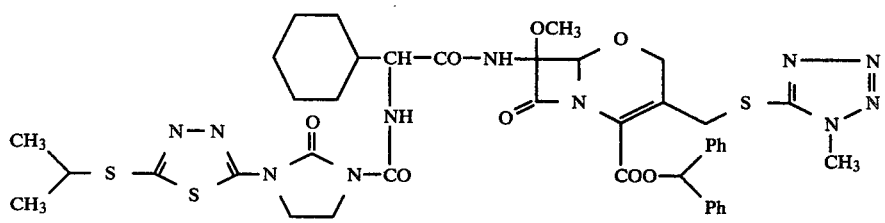

As described in Example 10, there were obtained from 241 mg 7-amino-7-methoxy-3-(1-methyl-1-H-tetrazol-5-yl-thiomethyl)-1-oxadethia-3-cephem-4-carboxylic acid diphenyl methyl ester and 353 mg 2-[2-oxo-3-(5-isopropylthio-1-thia-3,4-diazol-2-yl)-imidazolidin-1-yl]-carbonylamino-phenyl acetic acid after chromatography 50 mg 7-methoxy-7{D,L-[2-oxo-3-(5-isopropylthio-1-thia-3,4-diazol-2-yl)-imidazolidin-1-yl]-carbonylaminophenylacetamido}-1-oxadethia-3-cephem-4-carboxylic acid diphenyl methyl ester.

Mp.: 177° C. (Decomp.),
Rf: 0.47 (ethyl acetate).

$^1$H-NMR (250 MHz, CDCl$_3$)δ1.44, 1.47 (s, 6H, CH$_3$), 3.33, 3.52 (s, 3H, OCH$_3$), 3.85, 3.87 (s, NCH$_3$), 3.8 (m, CH), 4.0–4.3 (m, CH$_2$N, CH$_2$S), total 10H, 4.54 (m, 2H, CH$_2$O), 5.04, 5.08 (s, 1H, azetidinon—H), 5.52, 5.55 (d, J=7.5 Hz, 1H, NHCHCO), 6.52, 6.54 (s, 1H, NH), 6.89, 6.91 (s, 1H, CHPh$_2$), 7.2–7.6 (m, 15H, Ph), 8.95, 9.02 (d, J=7.5 Hz, 1H, CHNHCO).

EXAMPLE 27

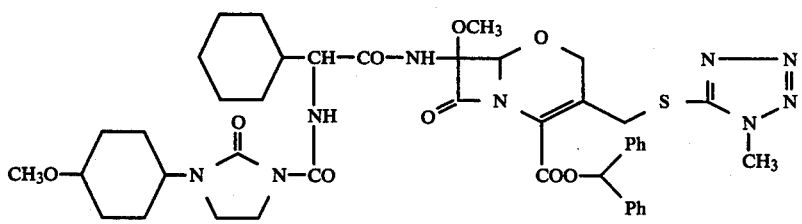

As described in Example 10, there were obtained from 4.07 g 7-amino-7-methoxy-3-(1-methyl-1-H-tetrazol-5-yl-thiomethyl)-1-oxadethia-3-cephem-4-carboxylic acid diphenyl methyl ester and 3.84 g 2-[2-oxo-3-(4-anisyl)-imidazolidin-1-yl]-carbonylaminophenyl acetic acid after chromatography on 500 g silica gel (ethyl acetate:toluene 65:45) 1.52 g 7-methoxy-7-{D,L-[2-oxo-3-(4-anisyl)-imidazolidin-1-yl]-carbonylamino-phenylacetamido}-3-(1-methyl-1-H-tetrazol-5-yl-thiomethyl)-1-oxadethia-3-cephem-4-carboxylic acid diphenyl methyl ester.

Mp.: 156° C. (Decomp.)
Rf=0.29 (ethylacetat:toluene 65:45).

$^1$H-NMR (250 MHz, CDCl$_3$)$\delta$3.36, 3.53 (s, 3H, OCH$_3$), 3.81, 3.83 (s, 6H, OCH$_3$, N—CH$_3$), 3.7–4.0 (m, 4H, CH$_2$N), 4.25, 4.5 (m, 4H, CH$_2$S, CH$_2$O), 5.03, 5.08 (s, 1H, azetidinon—H), 5.61, 5.67 (d, J=7 Hz, 1H, NHCHCO), 6.91 (d, J=8 Hz, anisyl—H), 6.91 (s, CHPh$_2$) zus. 3H, 7.2–7.6 (m, 17H, Ph, anisyl—H, NH), 9.24, 9.30 (d, J=7 Hz, CHNHCO).

IR (KBr) 3295 (NH, amide), 1787 (C=O, β-lactam), 1711 (C=O, ester), 1675 cm$^{-1}$ (C=O, amide).

EXAMPLE 28

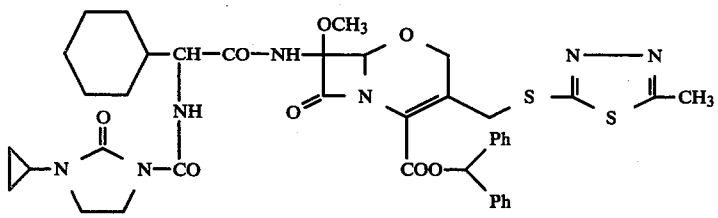

As described in Example 10 there were obtained from 370 mg 7-amino-7-methoxy-3-(2-methyl-1-thia-3,4-diazol-5-yl-thiomethyl)-1-oxadethia-3-cephem-4-carboxylic acid diphenyl methyl ester and 278 mg 2-(3-cyclopropyl-2-oxo-imidazolidin-1-yl)-carbonylaminophenyl acetic acid after chromatography (ethyl acetate) 123 mg 7-methoxy-7-[D,L-(3-cyclopropyl-2-oxo-imidazolidin-1-yl)-carbonylamino-phenylacetamido]-3-(2-methyl-1-thia-3,4-diazol-5-yl-thiomethyl)-1-oxadethia-3-cephem-4-carboxylic acid diphenyl-methyl ester.

Mp~190° C. (decomp.),
Rf=0.27 (ethyl acetate).

$^1$H-NMR (250 MHz, CDCl$_3$)$\delta$0.75 (m 4H, cyclopropyl—H), 2.50 (m, 1H, cyclopropyl—H), 2.71, 2.72 (s, 3H, CH$_3$), 3.4, 3.8 (m, CH$_2$N), 3.40, 3.53 (s. OCH$_3$) total 7H, 4.2–4.55 (m, 4H, CH$_2$S, CH$_2$O), 5.04, 5.08 (s, 1H, acetidinon—H), 5.53 (d, J=8 Hz, 1H, NHCHCO), 6.83, 6.87 (s, 1H, NH), 6.92, 6.94 (s, 1H, CHPh$_2$), 7.2–7.6 (m, 15H, Ph), 9.14 (d, J=8 Hz, 1H, CHNHCO).

IR (IBr) 1783(C=O, β-lactam), 1714 (C=O, ester), 1681 cm$^{-1}$ (C=O, amide).

EXAMPLE 29

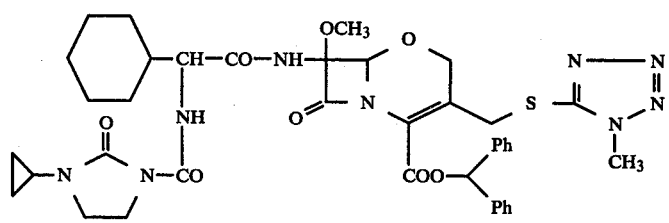

As described in Example 10 there were obtained from 2.54 g 7-amino-7-methoxy-3-(1-methyl-1-H-tetrazol-5-yl-thiomethyl)-1-oxadethia-3-cephem-4-carbonixylic acid diphenyl methyl ester and 1.97 g 2-(3-cyclopropyl-2-oxo-imidazolidin-1-yl)-carbonylamino-phenylacetic acid after chromatography (ethyl acetate:toluene 95:5) 1.62 g 7-methoxy-2-[D,L-(3-cyclopropyl-2-oxo-imidazolidin-1-yl)-carbonylamino-phenylacetamido]-3-(1-methyl-1-H-tetrazol-5-yl-thiomethyl)-1-oxadethia-3-cephem-4-carboxylic acid diphenyl methyl ester.

Mp: 151° C. (Decomp.),
Rf=0.36 (ethylacetate).

$^1$H-NMR (250 MHz, CDCl$_3$)$\delta$0.75 (m, 4H, cyclopropyl—H), 250 (m, 1H, cyclopropyl—H), 3.4, 3.8 (m, CH$_2$N), 3.43, 3.54 (s, OCH$_3$), 3.87, 3.89 (s, NCH$_3$) total 10H, 4.3 (m, 2H, CH$_2$S), 4.55 (m, 2H, CH$_2$O), 5.04, 5.09 (s, 1H, acetidinon—H), 5.48 (d, J=7 Hz, 1H, NHCHCO), 6.69, 6.78 (s, 1H, NH), 6.91, 6.95 (s, 1H, CHPh$_2$), 7.2–7.6 (m, 15H, Ph), 9.13 (d, J=7 Hz, 1H, CHNHCO).

IR (KBr) 1785 (C=O, β-lactam), 1715 (C=O, ester), 1660 cm$^{-1}$ (C=O, amide).

EXAMPLE 30

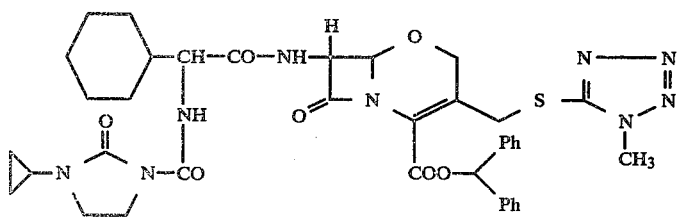

As described in Example 21 there was obtained from 441 mg 7-amino-3-(1-methyl-1-H-tetrazol-5-yl-thiomethyl)-1-oxadethia-3-cephem-4-carboxylic acid diphenyl methyl ester and 210 mg 2-(3-cyclopropyl-2-oxo-imidazolidin-1-yl)-carbonylamino-phenyl acetic acid after 3 hours at −20° C. and 4 hours at 0° C. 322 mg 7-[D,L-(3-cyclopropyl-2-oxo-imidazolidin-1-yl)-carbonylamino-phenylacetamido]-3-(1-methyl-1-H-tetrazol-5-yl-thiomethyl)-1-oxadethia-3-cephem-4-carboxylic acid diphenylmethyl ester as a powder.

Mp.: 148°–153° (Decomp.).

$^1$H-NMR (250 MHz, CDCl$_3$)δ0.75 (m, 4H, cyclopropyl—H), 2.50 (m, 1H, cyclopropyl—H), 3.5–3.8 (m, 4H, CH$_2$N), 4.98 (s, 1H, N—CH$_3$), 4.25 (m, 2H, CH$_2$S), 4.6 (m, 2H, CH$_2$O), 5.00 (d, J=4 Hz, 1H, acetidinon—H), 5.51 (dd, J=4 Hz, J=9 Hz, 1H, acetidinon—H), 5.66 (d, J=7.5 Hz, 1H, NHCHCO), 6.96 (s, 1H, CHPh$_2$), 7.2–7.7 (, 16H, Ph, NH), 9.14 (d, J=7.5 Hz, 1H, CHNHCO).

IR (KBr) 1782 (C═O, β-lactam), 1713 (C═O, ester), 1664 cm$^{-1}$ (C═O, amide).

SPLIT-OFF OF THE DIPHENYL METHYL ESTER-PROTECTING GROUP

As explicitly described in Examples 2, 5, 7, 9 and 11 the following acids were obtained from the above-synthesized corresponding diphenyl methyl ester

EXAMPLE 31 powder,

Mp.: above 146° C. (decomp.),

RF=0.28 (BABA)

$^1$H-NMR (250 MHz, DMSO)δ2.67, 2.69 (s, 3H, CH$_3$), 3.06, 3.32 (s, OCH$_3$), 3.4, 3.75 (m, CH$_2$N) total 7H, 5.05, 5.09 (s, 1H, H-6), 5.64 (d, J=7.5 Hz, 1H, NHCHCO), 6.62, 6.84 (m, 2H, furyl—H), 6.9–7.5 (m, 6H, C$_6$H$_5$, NH), 7.74, 7.84 (s, 2H, CH═N, furyl—H), 8.95, 9.11 (d, J=7.5 Hz, 1H, CHNHCO), 9.44, 9.48 (s, 1H, COOH).

IR (KBr)~3300 (b, OH), 1781 (C═O, β-lactam, 1680–1720 cm$^{-1}$ (C═O, acid, amide; C═N).

EXAMPLE 32

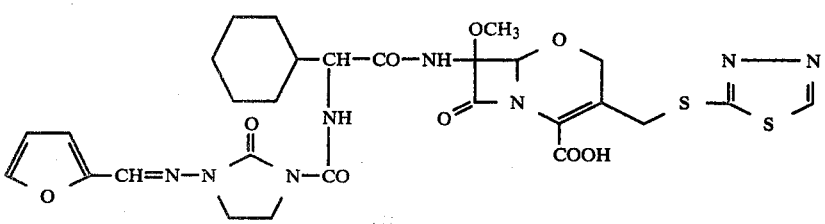

powder,

Mp.: from 143° C. (decomp.),

Rf=0.27 (BABA).

$^1$H-NMR (250 MHz, DMSO)δ3.06, 3.35 (s, OCH$_3$), 3.4, 3.75 (m, CH$_2$N), total 7H, 4.1–4.6 (m, 4H, CH$_2$S, CH$_2$O), 5.06, 5.09 (s, 1H, H-6), 5.63 (d, J=7.5 Hz, 1H, NHCHCO), 6.63, 6.84 (m, 2H, furyl—H), 6.9–7.5 (m, 6H, C$_6$H$_5$, NH), 7.74, 7.84 (s, 2H, CH═N, furyl—H), 8.95, 9.10 (d, J=7.5 Hz, 1H, CHNHCO). 9.44, 9.48 (s. 1H, COOH), 9.58, 9.60 (s, 1H, thiadiazol—H).

IR (KBr)~3300 (b, OH), 1780 (C═O, 0-lactam), 1660–1721 cm$^{-1}$ (C═O, acid, amide; C═N).

EXAMPLE 33

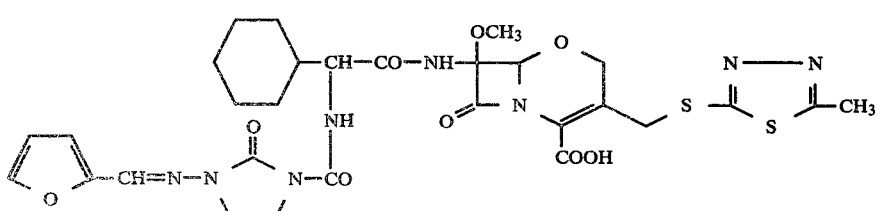

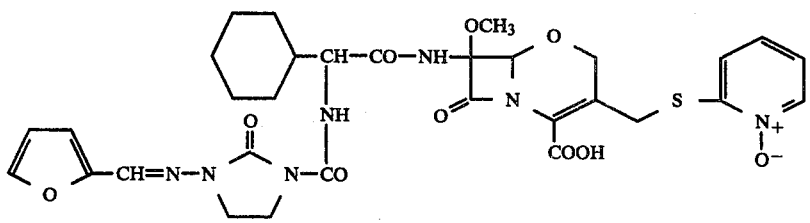

powder,
Mp.: from 148° C. (decomp.),
Rf=0.15 (BABA).
$^1$H-NMR (250 MHz, DMSO) 3.37 (s, OCH$_3$), 3.4, (m, CH$_2$N) total 7H, 3.9–4.5 (m, 4H, CH$_2$S, CH$_2$O), 5.13 (s, 1H, H-6), 5.65 (d, J=7.5 Hz, 1H, NHCHCO), 6.65, 6.86 (m, 2H, furyl—H), 7.2–7.5 (m, OH, C$_6$H$_5$, pyridyl—H, NH), 7.75, 7.86 (s, 2H, CH=N, furyl—H), 8.35 (d, J=8 Hz, 1H, pyridyl—H), 8.98 (d, J=75 Hz, 1H, CHNHCO), 9.50 (s, 1H, COOH).
IR (KBr) 3500–3100 (b, OH), 3300 (NH), 1785 (C=O, β-lactam), 1725 (C=O, acid), 1680 cm$^{-1}$ (C=O, amide; C=N).

Yellow powder,
Mp.: from 154° C. (decomp.),
Rf=0.3 (BABA).
$^1$H-NMR (250 MHz, DMSO) 2.50 (s, CH$_3$SO—), 3.4, 4.3 (m, 4H, CH$_2$N), 3.85 (s, 3H, NCH$_3$), 4.2–4.6 (m, 4H, CH$_2$S, CH$_2$O), 5.03 (d, J=4 Hz, 1H, H-6), 5.67 (dd, J=4 Hz, J=9 Hz, 1H, H-7), 5.85 (d, J=7.5 Hz, 1H, NHCHCO), 6.63, 6.87 (m, 2H furyl—H), 6.9–7.5 (m, 6H, C$_6$H$_5$, NH), 7.7 (s, 1H, CH=N), 8.97 (d, J=7.5 Hz, 1H, CHNHCO), 9.59 (s, 1H, COOH).
IR (KBr) 3500–3100 (b, OH), 3306 (NH), 1783 (C=O, β-lactam), 1728 (C=O, acid), 1690 (C=O, amide; C=N).

EXAMPLE 34

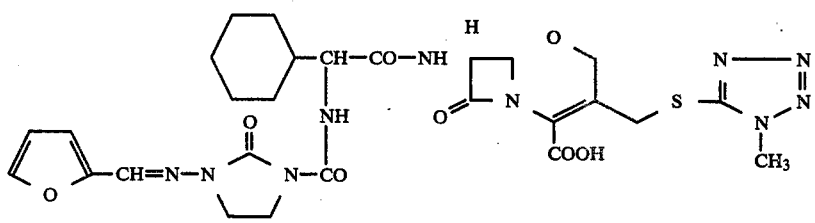

colorless powder
$^1$H-NMR (250 MHz, DMSO)δ3.75–3.85 (m, CH$_2$N), 3.95 (s, 3H, N—CH$_3$), 4.17, 4.39 (AB-signal, J=12.5 Hz, 2H, CH$_2$S), 4.43, 4.68 (AB-signal, J=18.5 Hz, 2H, CH$_2$O), 5.01 (d, J=4 Hz, 1H, H-6), 5.69 (dd, J=4 Hz, J=9 Hz, 1H, H-7), 5.67 (d, J=7.5 Hz, 1H, NHCHCO), 6.51, 6.81 (m, 2H, furyl—H), 7.3–7.6 (m, 6H, C$_6$H$_5$, furyl—H), 7.72 (s, 1H, CH=N), 8.42 (d, J=9 Hz, 1H, NH) 9.17 (d, J=7.5 Hz, 1H, CHNHCO).

EXAMPLE 35

EXAMPLE 36

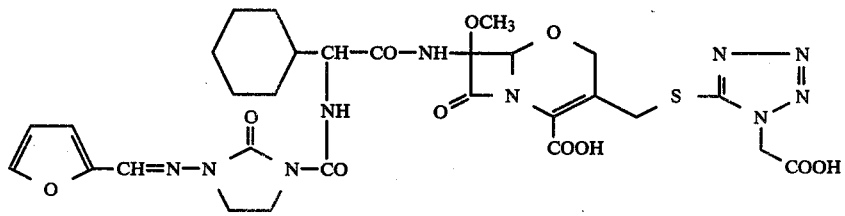

light brown powder,
Mp.: from 139° C. (sintering) from 159° C. (decomp.).
$^1$H-NMR (250 MHz, DMSO)δ3.06, 3.37 (s, OCH$_3$), 3.4, 3.8 (m, CH$_2$N), zus. 7H, 4.2–4.6 (m, 4H, CH$_2$S, CH$_2$O), 5.0 (s, 2H, N—CH$_2$—COO), 5.06, 5.10 (s, 1H, H-6), 5.65 (d, J=7 Hz, 1H, NHCHCO), 6.63, 6.88 (m, 2H, furyl—H), 7.0–7.5 (m, 6H, C$_6$H$_5$, furyl—H), 7.80 (s, 1H, CH=N), 7.87 (s, 1H, NH), 9.0, 9.1 (d, J=7 Hz, 1H, CHNHCO).

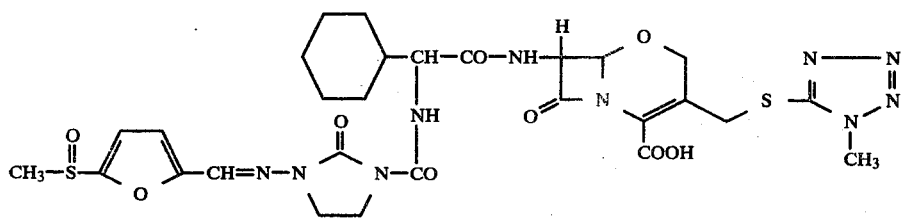

CHNHCO), 9.3 (s, 1H, COOH), 9.5, 0.503 (s, 1H, COOH).

IR (KBr) 3550–3050 (b, OH), 1876 (C=O), β-lactam, 1725, 1710 (C=O, acid), 1680 cm⁻¹ (sh, C=O, amide; C=N).

EXAMPLE 37

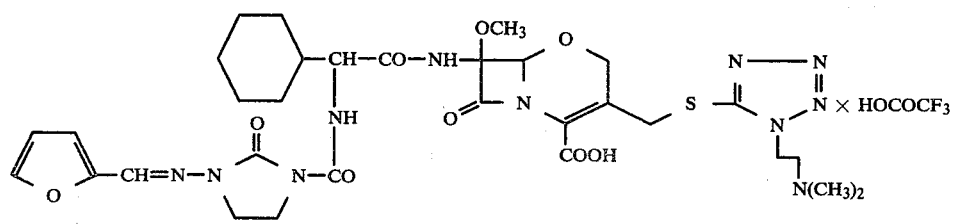

light powder
¹H-NMR (250 MHz, DMSO-D₂O)δ3.1 (s, 6H, NCH₃), 3.3, 3.5 (s, OCH₃), 3.6 (t, CH₂N), zus. 5H, 3.7–4.8 (m, 10H, CH₂S, CH₂O, CH₂N), 5.01, 5.08 (s, 1H, H-6), 5.7 (m, 1H, NHCHCO), 6.5, 6.8 (m, 2H, furyl—H), 7.0–7.6 (m ~9H, C₆H₅, furyl—H, CH=N).

IR (KBr) 3600–3000 (b, OH), 1780 (C=O, β-lactam).

EXAMPLE 38

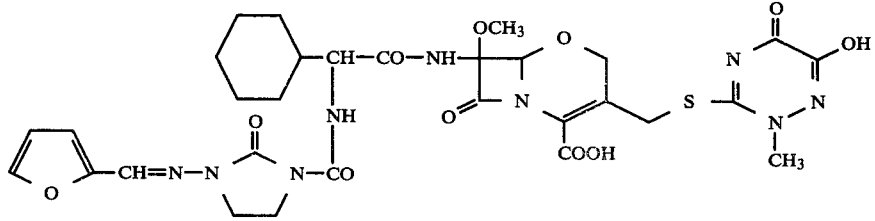

light yellow powder
¹H-NMR (250 MHz, DMSO-D₂O) 3.3, 3.5, 3.55 (s, 6H, OCH₃, NCH₃), 3.5–4.6 (m, CH₂S, CH₂N, CH₂O), 5.7 (bs, 1H, NHCHCO), 6.5, 6.8 (m, 2H, furyl—H), 7.2–7.7 (m, 7H, C₆H₅, furyl—H, CH=N).

IR (KBr) 1783 (C=O, β-lactam), 1775 (sh) 1590 cm⁻¹.

EXAMPLE 39 colorless powder,
Mp.: from 150° C. (decomp.),
Rf=0.35 (BABA).
¹H-NMR (250 MHz, CDCl₃-DMSO) 2.01, 2.04, (s, 3H, OCOCH₃), 3.97, 3.38 (s, OCH₃), 3.3–3.9 (m, CH₂N), total. 7H, 4.3–4.8 (m, 4H, CH₂O), 5.05, 5.10 (s, 1H, H-6), 5.65 (m, 1H, NHCHCO), 6.51, 6.82 (m, 2H furyl—H), 7.2–7.5 (m, 5H, C₆H₅), 7.77 (s, 1H, CH=N), 7.87 (bs, 1H, furyl—H), 9.0, 9.1 (d, J=7 Hz, 1H, CHNHCO), 9.48. 9.50 (s, 1H).

EXAMPLE 40

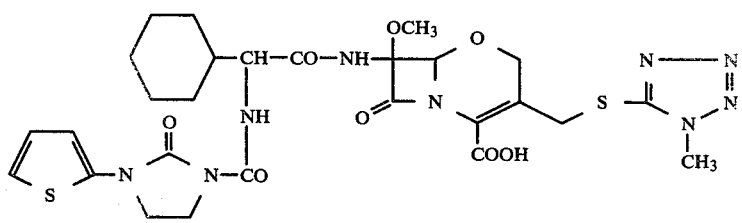

light powder
Mp.: from 171° C. (decomp),
Rf=0.4 (BABA).
¹H-NMR (250 MHz, DMSO) δ 3.06, 3.34 (s, 3H, OCH₃), 3.91, 3.94 (s, NCH₃), 3.7–4.5 (m, CH₂N, CH₂S, CH₂O), total 11H, 5.03, 5.05 (s, 1H, H-6), 5.6 (m, 1H, NHCHCO), 6.4–7.5 (m, 9H, C₆H₅, NH, thienyl—H), 8.98, 9.03 (d, J=7.5 Hz, 1H, CHNHCO), 9.46 (bs, 1H, COOH).

IR (KBr) 3600–3100 (b, OH), 3300 (NH), 1786 (C=O, β-lactam), 1712 (C=O, acid), 1680 cm⁻¹ (sh, C=O, amide, C=N).

EXAMPLE 41

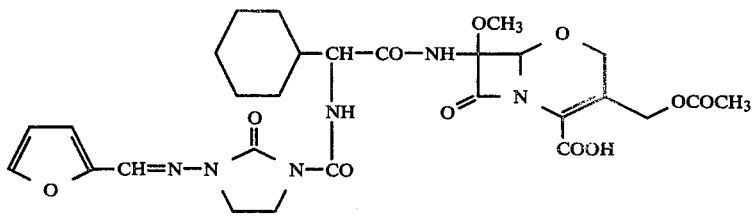

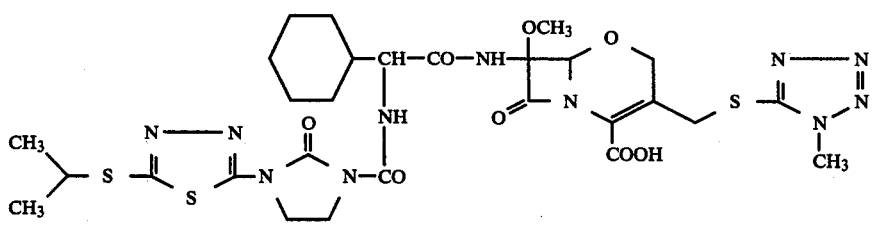

powder,
Mp.: from 174° C. (decomp.),
Rf=0.3 (BABA).
$^1$H-NMR (250 MHz, CDCl$_2$-DMSO) δ 1.44, 1.47 (s, 6H, CH$_3$), 3.1, 3.4 (s, OCH$_3$), 3.89 (s, NCH$_3$), 3.0–4.5 (m, CH$_2$N, CH$_2$S, CH$_2$O, CH), total 13H, 4.98 (bs, 1H, H-6), 5.52, 5.64 (d, J=7 Hz, 1H, NHCHCO), 6.49 (s, 1H, NH), 7.2–7.6 (m, 5H, C$_6$H$_5$), 8.9, 9.1 (m).
IR (KBr) 3600–3100 (b, OH), 3330 (NH), 1774 (C=O, β-lactam), 1720 (C=O, acid), 1677 cm$^{-1}$ (C=O, amide; C=N).

EXAMPLE 42

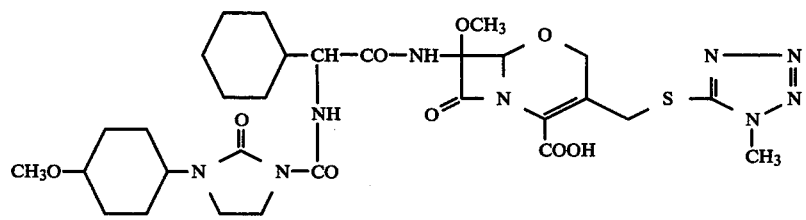

Colorless powder,
Mp.: from 160° C. (decomp.),
Rf=0.38 (BABA).
$^1$H-NMR (250 MHz, DMSO) δ 3.08, 3.37 (s, OHC$_3$), 3.4 (m, CH$_2$N), total 5H, 3.76 (s, OCH$_3$), 3.93, 3.95 (s, NCH$_3$), 3.7–4.0 (m, CH$_2$N), total 8H, 4.2–4.55 (m, 4H, CH$_2$S, CH$_2$O), 5.05–5.08 (s, 1H, H-6), 5.67 (d, J=9 Hz, 1H, NHCHCO), 6.85–7.55 (m, 10H, NH, H aromat.), 9.03, 9.19 (d, J=9 Hz, 1H, CHNHCO), 9.46, 9.48 (s, 1H, COOH).

IR (KBr 3500–3150 (b, OH), 1784 (C=O, β-lactam), 1708 (C=O, acid), 1675 cm$^{-1}$ (sh, C=O, amide; C=N).

EXAMPLE 43

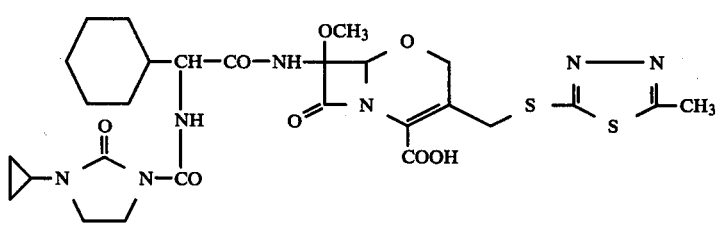

powder,
Mp.: from 155° C. (decomp.),
Rf=0.2 (BABA)
$^1$H-NMR (250 MHz, DMSO) 0.70 (m, 4H, cyclopropyl—H), 2.5 (m, cyclopropyl—H under DMSO), 3.11, 3.39 (s, OCH$_3$), 3.3–3.7 (m, CH$_2$N), total 7H, 4.2–4.6 (m, 4H, CH$_2$S, CH$_2$O), 5.09, 5.11 (s, 1H, H-6), 5.65 (d, J=8 Hz, 1H, NHCHCO), 7.1–7.5 (m, 5H, C$_6$H$_5$), 9.01 (d, J=8 Hz, 1H, NH), 9.16, 9.20 (s, 1H, NH), 9.44, 9.47 (s, 1H, COOH).
IR (KBr) 3600–3100 (b, OH), 1783 (C=O, β-lactam), 1711 (C=O, acid), 1675 cm$^{-1}$ (C=O, amide; C=N).

EXAMPLE 44

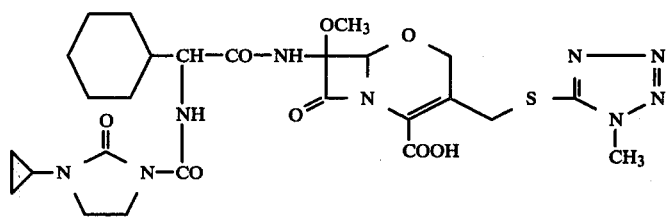

powder,
Mp.: from 146° C. (decompl.),
Rf=0.2 (BABA)
$^1$H-NMR (250 MHz, DMSO) δ0.65 (m, 4H, cyclopropyl—H), 2.5 (m, cyclopropyl—H under DMSO), 3.07, 3.35 (s, OCH$_3$), 3.3–3.8 (m, CH$_2$N), total 7H, 3.94, 3.96 (s, 3H, NCH₃), 4.2–4.5 (m, 4H, CH₂S, CH₂O), 5.05, 5.08 (s, 1H, H-6), 5.61 (d, J=9 Hz, 1H, NHCHCO), 6.9–7.5 (m, 6H, C₆H₅, NH), 8.98, 9.15 (d, J=9 Hz, 1H, CHNHCO), 9.45 (bs, 1H, COOH).

IR (KBr) 3600–3100 (b, OH), 3300 (NH), 1787 (C=O, β-lactam), 1712 (C=O, acid), 1675 cm⁻¹ (sh, C=O, amide; C=N).

EXAMPLE 45

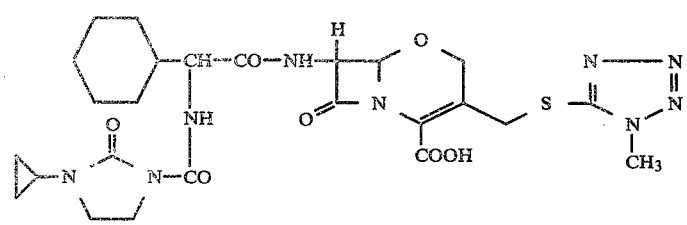

light powder,
Mp.: from 143° C. (decomp.),
Rf=0.23 (BABA)

¹H-NMR (250 MHz, DMSO) δ0.69 (m, 4H, cyclopropyl—H), 2.5 (m, cyclopropyl—H under DMSO), 3.25–3.8 (m, CH₂N), total 7H, 3.95 (s, 3H, NCH₃), 4.2–4.6 (m, 4H, CH₂S), CH₂O), 5.1 (d, J=4 Hz, 1H, H-6), 5.5 (dd, J=4 Hz, J=9 Hz, 1H, H-7), 5.64 (d, J=8 Hz, 1H, NHCHCO), 7.1–7.5 (m, 6H, C₆H₅, NH), 9.0, 9.1 (d, J=8 Hz, 1H, CHNHCO), 9.48 (s, 1H, COOH).

IR (KBr) 3500–3100 (b, OH), 1784 (C=O, β-lactam), 1710 (C=O, acid), 1780 cm⁻¹ (sh, C=O, amide; C=N).

EXAMPLE 46

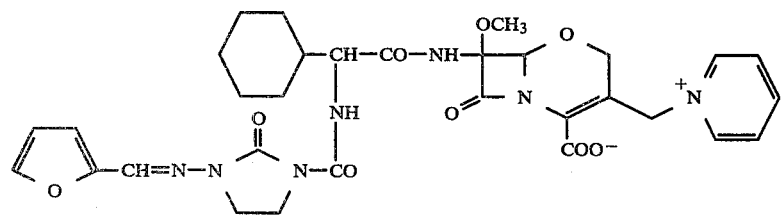

To a suspension of 687 mg 7-methoxy-7-[(2-oxo-3-furfurylideneamino-imidazolidin-1-yl)-carbonylamino-phenylacetamido]-3-acetoxymethyl-1-oxadethia-3-cephem-4-carboxylic acid in 5.8 ml water, 42 mg NaHCO₃, then 285 μl pyridine and 2.3 g potassiumthiocyanate were added. With 6 N HCl the pH was adjusted to 6.5 and the mixture was warmed up to 60° C. for 7 hours. After cooling 12 ml of water were added, undissolved material was filtered off and the filtrate was chromatographed on Diaion (RTM) HP-20. (a-H₂O, b-H₂O:MeOH 1:1). The solvent was evaporated under vacuum and the residue was washed with a little methanol. 129 mg 7-methoxy-7-[(2-oxo-3-furfurylideneamino-imidazolidin-1-yl)-carbonylamino-phenylacetamido]-3-(1-pyridinomethyl)-1-oxadethia-3-cephem-4-carboxylate were obtained as a powder.

Rf=0.3 (CH₃CN:H₂O).

¹H-NMR (250 MHz, DMSO-D₂O) δ3.1, 3.3 (s, OCH₃), 3.3–4.0 (m, CH₂N), total 7H, 4.3–4.5 (m, 2H, CH₂O), 4.98, 5.03 (s, 1H, H-6), 5.15–5.45 (m, 2H, CH₂N⊕), 5.66 (m, 1H, NHCHCO), 7.0–7.6 (m, 1H, 4-pyridyl—H), 8.78 (d, J=7 Hz, 2H, 2-pyridyl—H).

It will be appreciated that the instant specification and examples are set forth by way of illustration and not limitation, and that various modifications and changes may be made without departing from the spirit and scope of the present invention.

EXAMPLE 47

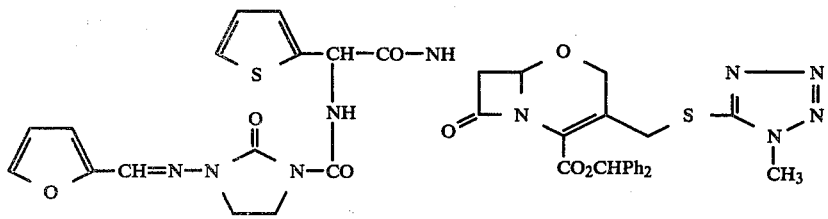

As described in Example 10 one obtains from 924 mg 7-amino-3-(1-methyl-1-H-tetrazol-5-yl-thiomethyl)-1-oxadethia-3-cephem-4-carboxylic acid diphenyl methyl ester and 940 mg 2-(2-oxo-3-furfurylideneamino-imidazolidin-1-yl)-carbonylamino-thienyl acetic acid after 6 h at 0° C. and chromatography (ethylacetate) 412 mg of the corresponding oxacephem as an off white hard foam.

¹H-NMR (250 MHz, CDCl₃) δ3.91 (s, 3H, N—CH₃), 3.9, 4.1 (m, 4H, CH₂N), 4.29, 4.38 (AB-Signal, J=12 Hz, 2H, CH₂S), 4.59, 4.85 (AB-Signal, J=16 Hz, 2H, CH₂O), 5.14 (d, J=4.5 Hz, 1H, H-6), 5.82 (dd, J=4.5 Hz, J=8 Hz, H-7), 5.86 (d, J=9 Hz, NHCHCO), together 2H, 6.58, 6.88 (m, Furyl—H), 6.97 (s, 1H, CHPh₂), 7.0–7.6 (m, 15-H, C₆H₅, Furyl—H, Thienyl—H, NH), 7.83 (s, 1H, CH=N), 9.13 (d, J=8 Hz, 1H, CHNHCO).

EXAMPLE 48

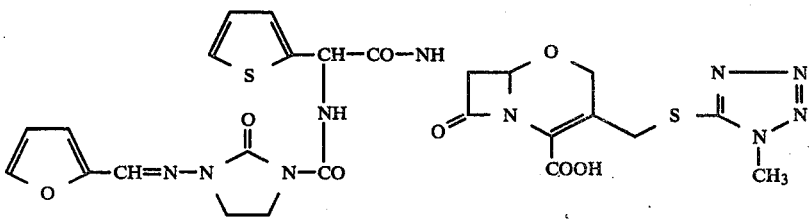

As described in Example 11 the above acid was obtained from the corresponding diphenyl methyl ester (Example 47) as a powder.

$^1$H-NMR (250 MHz, DMSO) δ3.7–4.0 (m, 4H, CH$_2$N), 4.0 (s, 3H, N—CH$_3$), 4.22, 4.36 (AB-Signal, J=14 Hz, 2H, CH$_2$S), 4.59, 4.72 (AB-Signal, J=17.5 Hz, 2H, CH$_2$O), 5.20 (d, J=4.5 Hz, 1H, H-6), 5.65 (dd, J=4.5 Hz, J=10 Hz, 1H, H-7), 5.98 (d, J=9 Hz, 1H, NHCHCO), 6.64, 6.86 (m, 2H, Furyl—H), 7.01, 7.13, 7.46 (m, 3H, Thienyl—H), 7.78 (s, CH=N), 7.82 (m, Furyl—H), together 2H, 9.08 (d, J=9 Hz, 1H, NHCHCO), 9.39 (d, J=10 Hz, 1H, NH).

IR (KBr): ~3400 (b, OH), 1777 (C=O, β-Lactam), 1722 (C=O, acid), 1680 cm$^{-1}$ (C=O, amide, C=N).

What is claimed is:

1. A β-lactam of the formula

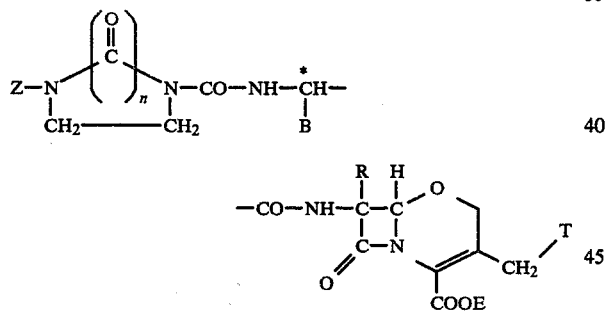

or a hydrate thereof,
in which
R represents a hydrogen atom or a methoxy group,
n is 1 or 2,
Z represents a group of the formula

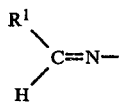

wherein R$^1$ denotes a phenyl group which is optionally substituted by halogen, alkyl or alkoxy having 1 to 4 carbon atoms, nitro, cyano, 1 or 2 hydroxyl groups, S-alkyl having 1 to 4 carbon atoms, alkylsulphonyl having 1 to 4 carbon atoms or CH$_3$OOC—; or denotes a thienyl or furyl group which is optionally substituted by halogen, NO$_2$, alkyl or alkoxy-carbonyl having 1 to 4 carbon atoms, S—C$_1$ to C$_4$ alkyl, C$_1$ to C$_4$ alkylsulphonyl, C$_1$ to C$_4$-alkyl-sulphinyl or CH$_3$COOCH$_2$—, or denotes a pyridyl group;

or, when n is 1,

Z can also represent a cyclopropyl, furyl, pyridyl, thienyl, or benzthiazol-2-yl radical, or a 1, 3, 4-thiadiazol-2-yl radical which is optionally substituted in the 5-position by sec.-butyl, trifluoromethyl, methylthio, i-propylthio or methylsulphonyl, B represents a phenyl, hydroxyphenyl, cyclohexadienyl, furyl, thienyl, pyrrolyl, imidazolyl, thiazolyl, isothiazolyl, isoxazolyl or thiadiazolyl group, T denotes an alkyl—CO—O—, pyridinium, aminopyridinium, carbamoylpyridinium or carbamoyloxy group, an —S—phenyl group which can be substituted, or a tetrazolylthio or thia-diazolylthio group which is optionally substituted by alkyl having 1 to 4 carbon atoms, by CF$_3$ or by CH$_2$COOH; and E represents a hydrogen atom, a pharmaceutically acceptable ester grouping, a salt-forming cation or a protective group, or represents a negative charge when T contains a quaternary nitrogen.

2. A compound or hydrate according to claim 1, in which R represents a methoxy group, T represents —OCOCH$_3$, or a tetrazolylthio or thiadiazolylthio group which is optionally substituted by alkyl having 1 to 4 carbon atoms, by CF$_3$ or by CH$_2$COOH, or represents a pyridinium, aminopyridinium, carbamoylpyridinium, carbamoyloxy or 1, 2, 5, 6-tetrahydro-2-methyl-5,6-dioxo-asym-triazin-3-ylthio group and C* is present in the D—=R configuration.

3. A compound or hydrate according to claim 2, in which

R$^1$ denotes a phenyl group which is optionally substituted by fluorine, chlorine, bromine, methyl, methoxy, nitro, cyano, 1 or 2 hydroxyl groups, S-methyl, methylsulphonyl or CH$_3$OOC—; denotes a thienyl or furyl group bonded in the 2-position or 3-position and optionally substituted in the 4-position or 5-position by chlorine, bromine, NO$_2$, alkyl or alkoxycarbonyl having 1 to 4 carbon atoms, S—C$_1$ to C$_4$ alkyl, methylsulphonyl, methylsulphinyl or CH$_3$COOCH$_2$—; or denotes a pyrid-3-yl group.

4. A compound according to claim 1, wherein such compound is 7-methoxy-7-(α-2-oxo-3-(4-methyl-sulphinylfurfurylidene)-amino-imidazolidin-1-yl)-carbonyl-amino-thienylacetamido)-3-(1-methyl-1-H-tetrazol-5-yl-thiomethyl)-1-oxadethia-3-cephem-4-carboxylic acid of the formula

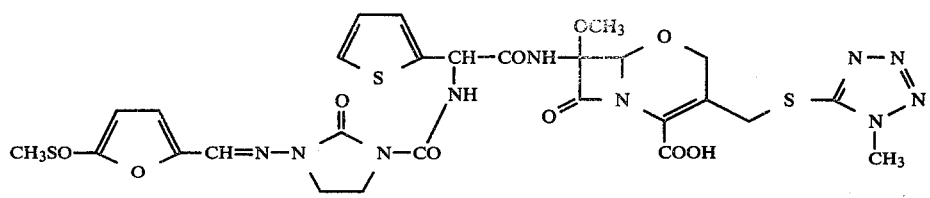

5. A compound according to claim 1, wherein such compound is 7-methoxy-7-[(2-oxo-3-furfurylideneamino-imidazolidin-1-yl)-carbonylamino-phenylacetamido]-3-(1-methyl-1-H-tetrazol-5-yl-thiomethyl)-1-oxodethia-3-cephem-4-carboxylic acid of the formula

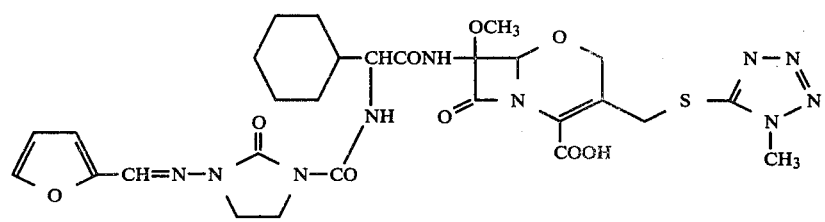

6. A compound according to claim 1, wherein such compound is 7-[(2-oxo-3-furfurylideneamino-imidazolidin-1-yl)-carbonylamino-phenylacetamido]-3-)-1-methyl-1-H-tetrazol-5-yl-thiomethyl)-1-oxadethia-3-cephem-4-carboxylic acid of the formula

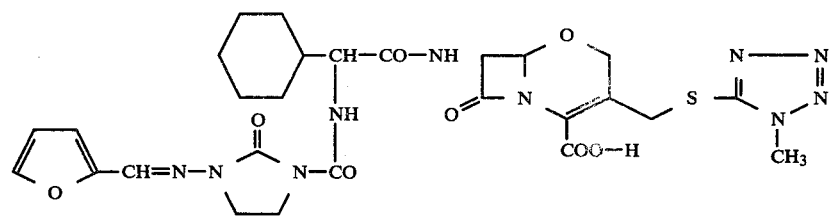

7. A compound according to claim 1, wherein such compound is 7-methoxy-7-[(2-oxo-3-furfurylideneamino-imidazolidin-1-yl)-carbonylamino-phenylacetamido]-3-(1-carboxymethyl-1-H-tetrazol-5-yl-thiomethyl)-1-oxadethia-3-cephem-4-carboxylic acid of the formula

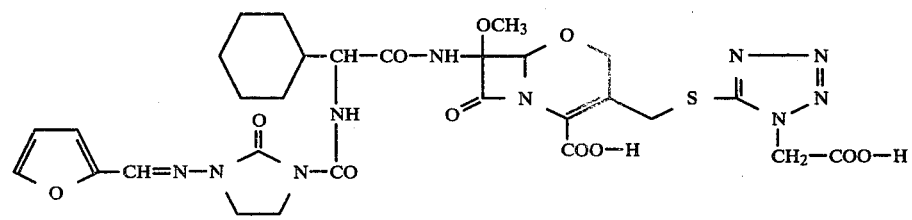

8. An antibacterial composition containing as an active ingredient an antibacterially effective amount of a compound or hydrate according to claim 1 in admixture with a diluent.

9. A composition according to claim 8 in dosage unit form in the form of a tablet, pill, dragee, capsule, ampoule, or suppository.

10. Drinking water, a feed or a feed formulation containing a growth-promoting effective amount of a compound or hydrate according to claim 1.

11. A method of combating bacterial illnesses in human and non-human animals which comprises administering to the animals an antibacterially effective amount of a compound or hydrate according to claim 1.

12. The method according to claim 11, wherein such compound is
7-methoxy-7-(α-2-oxo-3-(4-methyl-sulphinylfurfurylidene)-amino-imidazolidin-1-yl)-carbonyl-amino-thienylacetamido)-3-(1-methyl-1-H-tetrazol-5-yl-thiomethyl)-1-oxadethia-3-cephem-4-carboxylic acid,
7-methoxy-7-[(2-oxo-3-furfurylideneamino-imidazolidin-1-yl)-carbonylamino-phenylacetamido]-3-(1-methyl-1-H-tetrazol-5-yl-thiomethyl)-1-oxadethia-3-cephem-4-carboxylic acid,
7-[(2-oxo-3-furfurylideneamino-imidazolidin-1-yl)-carbonyl-amino-phenylacetamido]-3-)-1-methyl-1-H-tetrazol-5-yl-thiomethyl)-1-oxadethia-3-cephem-4-carboxylic acid, or
7-methoxy-7-[(2-oxo-3-furfurylideneamino-imidazolidin-1-yl)-carbonylamino-phenylacetamido]-3-(1-carboxymethyl-1-H-tetrazol-5-yl-thiomethyl)-1-oxadethia-3-cephem-4-carboxylic acid,
or a salt, ester or hydrate thereof.

* * * * *

UNITED STATES PATENT AND TRADEMARK OFFICE
CERTIFICATE OF CORRECTION

PATENT NO. : 4,438,114  
DATED : March 20, 1984  
INVENTOR(S) : Michael Boberg et al Page 1 of 6

It is certified that error appears in the above-identified patent and that said Letters Patent is hereby corrected as shown below:

| | |
|---|---|
| Under "U.S. Patent Documents" | 1st line delete "König" and substitute --Konig--; 2nd line delete "Feyer" and substitute --Feyen--; 3rd line delete "7/1980" and substitute --7/1982-- |
| Abstract, lines 7 and 13 | Delete "n" and substitute --n-- |
| Col. 5, line 12 | Delete "orr" and substitute --or-- |
| Col. 7, line 63 | Delete "bondded" and substitute --bonded-- |
| Col. 8, line 31 | Before "-SO$_2$" delete "CH$_2$" and substitute --CH$_3$-- |
| Col. 10, line 15 | Delete " $\underset{CH_3}{\overset{|}{\phantom{C}}}$ - COOH " and substitute -- $\underset{CH_2}{\overset{|}{\phantom{C}}}$ - COOH -- |
| Col. 11, lines 62, 63 | Delete "Enterobacteriacease" and substitute --Enterobacteriaceae-- |
| Col. 12, line 28 | Delete "bacterial" and substitute --bacteria-- |
| Col. 12, line 47 | Delete "curved" and substitute --cured-- |
| Col. 13, line 8 | Delete "formed" and substitute --form-- |
| Col. 17, line after "Example 3"; Col. 18, line after Example 4"; and Col. 19, line after "Example 5" | Delete "  " and substitute --  -- |

UNITED STATES PATENT AND TRADEMARK OFFICE
CERTIFICATE OF CORRECTION

PATENT NO. : 4,438,114

DATED : March 20, 1984

INVENTOR(S) : Michael Boberg et al

Page 2 of 6

It is certified that error appears in the above-identified patent and that said Letters Patent is hereby corrected as shown below:

Col. 23, line 1; Col. 24, line after "Example 11", Col. 25, line 1; Col. 25, after "Example 13"; Col. 27, line 1; Col. 27, line after "Example 15"; Col. 29, line 1; Col. 30, line after "Example 17"; Col. 31, line 1; Col. 31, line after Example 19; Col. 33, line 1; Col. 33, line after "Example 22"; Col. 34, line after "Example 23"; Col. 35, line 1; Col. 35, line after "Example 25"; Col. 36, line after "Example 26"; Col. 37, top of column; Col. 37, line after "Example 28"; Col. 38, line after "Example 29"; Col. 39, line 1; Col. 39, line 59 after "Example 31"; Col. 40, line after "Example 32"; Col. 41, line 1; Col. 41, line 26; Col. 41, line 56; Col. 42, line after "Example 36"; Col. 43, line after "Example 37"; Col. 43, line after "Example 38"; Col. 43, line after "Example 39"; Col. 44, line after "Example 40"; Col. 45, line 1; Col. 45, line after "Example 42"; Col. 46, line after "Example 43"; Col. 46, line after "Example 44"; Col. 47, line after "Example 45"; Col. 47, line after "Example 46"; Col. 51, line 17; Col. 51, line 32 and Col. 51, line 49

Delete "  " and substitute

--  --

UNITED STATES PATENT AND TRADEMARK OFFICE
CERTIFICATE OF CORRECTION

PATENT NO. : 4,438,114

DATED : March 20, 1984

INVENTOR(S) : Michael Boberg et al

Page 3 of 6

It is certified that error appears in the above-identified patent and that said Letters Patent is hereby corrected as shown below:

| | |
|---|---|
| Col. 19, line 45 | Delete "258" and substitute --2.58-- |
| Col. 24, line 18 | Delete "CHNHCO" and substitute --CHNHCO-- |
| Col. 24, line 61; Col. 25, line 46; Col. 26, line 47; Col. 27, line 46; Col. 28, line 46; Col. 29, line 65; Col. 32, line 21; Col. 32, line 51; Col. 33, line 39 | Delete "NHCHCO" and substitute --NHCHCO-- |
| Col. 27, line 50 and Col. 49, lines 26 and 29 | Delete "NHCHCO" and substitute --NHCHCO-- |
| Col. 31, Example 19, Middle of Structure | Insert --\ -- as follows: 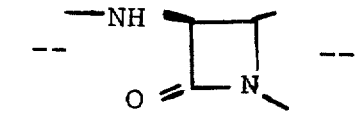 |
| Col. 32, line 23 | After "NH)" insert --,-- |
| Col. 32, line 24; Col. 32, line 66; Col. 33, line 42; Col. 33, line 19; Col. 34, line 63; Col. 35, line 39; Col. 36, line 19; Col. 36, line 66; Col. 37, line 41; Col. 38, line 20; Col. 38, line 65; Col. 39, line 46; Col. 40, line 22; Col. 40, line 48; Col. 41, line 20; Col. 41, line 20; Col. 41, line 55; Col. 42, line 21; Col. 43, line 1; Col. 44, line 21; Col. 44, line 52; Col. 45, line 67; Col. 47, | Delete "CHNHCO" and substitute --CHNHCO-- |

UNITED STATES PATENT AND TRADEMARK OFFICE
CERTIFICATE OF CORRECTION

PATENT NO. : 4,438,114

DATED : March 20, 1984

INVENTOR(S) : Michael Boberg et al

It is certified that error appears in the above-identified patent and that said Letters Patent is hereby corrected as shown below:

line 3 and Col. 47, line 41.

| | |
|---|---|
| Col. 32, line 51; Col. 33, line 39; Col. 34, line 17; Col. 34, line 61; Col. 36, line 65; Col. 37, line 39; Col. 38, line 18; Col. 38, line 63; Col. 39, line 44; Col. 40, line 19; Col. 40, line 46; Col. 41, line 16; Col. 41, line 53; Col. 42, line 19; Col. 42, line 53; Col. 43, line 51; Col. 44, line 7; Col. 44, line 51; Col. 45, line 29; Col. 45, line 66; Col. 46, line 34; Col. 47, line 2; Col. 47, line 40; Col. 48, line 9; and Col. 48, line 62 | Delete "NHCHCO" and substitute --NH<u>C</u>HCO-- |
| Col. 36, line 16 | Delete "5.65" and substitute --5.64-- |
| Col. 36, line 18; Col. 36, line 66; Col. 37, line 40; Col. 38, line 19; Col. 38, line 64 and Col. 48, line 64 | Delete "CHPh$_2$" and substitute --<u>C</u>HPh$_2$-- |
| Col. 37, line 1 | Delete "  " and substitute --  -- |
| Col. 37, line 2 | Delete "CH$_3$O— " and substitute -- CH$_3$O— -- |

UNITED STATES PATENT AND TRADEMARK OFFICE
CERTIFICATE OF CORRECTION

PATENT NO. : 4,438,114
DATED : March 20, 1984
INVENTOR(S) : Michael Boberg et al It is certified that error appears in the above-identified patent and that said Letters Patent is hereby corrected as shown below:

| | |
|---|---|
| Col. 38, line 16 | After "s" delete "," and substitute --.-- |
| Col. 38, line 21 | Delete "(C=O)," and substitute --(C=O,-- |
| Col. 39, line 54 | After "ester" insert --:-- |
| Col. 41, line 26 | Middle of formula insert lines: 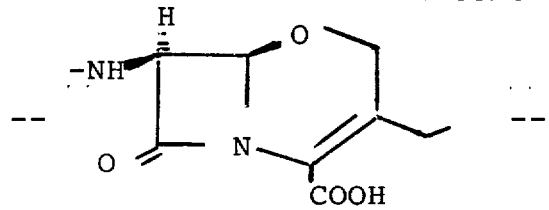 |
| Col. 43, line 34 | After "m" insert --,-- |
| Col. 45, line 45 | Insert ring in formula as follows: 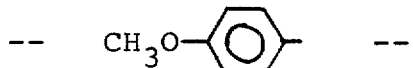 |
| Col. 45, line 50 | Delete "OHC₃)" and substitute --OCH₃)-- |
| Col. 47, line 62 | After "6" delete "N" and substitute --N-- |
| Col. 48, line after Ex. 47, Middle of formula ; Col. 49, line 1, and Col. 51, line 32 | Insert --\-- as follows: 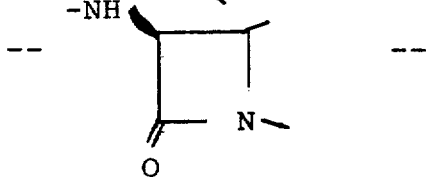 |

UNITED STATES PATENT AND TRADEMARK OFFICE
CERTIFICATE OF CORRECTION

PATENT NO. : 4,438,114
DATED : March 20, 1984
INVENTOR(S) : Michael Boberg et al It is certified that error appears in the above-identified patent and that said Letters Patent is hereby corrected as shown below:

Col. 50, line 19            Delete "n" and substitute --$\underline{n}$--

Signed and Sealed this

Nineteenth Day of March 1985

[SEAL]

*Attest:*

*Attesting Officer*

DONALD J. QUIGG

*Acting Commissioner of Patents and Trademarks*